(12) United States Patent
Pillai

(10) Patent No.: US 12,042,152 B2
(45) Date of Patent: *Jul. 23, 2024

(54) SYSTEMS AND METHODS FOR RETROGRADE PERFUSION AND CLEARANCE OF EMBOLI

(71) Applicant: Lakshmikumar Pillai, Morgantown, WV (US)

(72) Inventor: Lakshmikumar Pillai, Morgantown, WV (US)

( * ) Notice: Subject to any disclaimer, the term of this patent is extended or adjusted under 35 U.S.C. 154(b) by 312 days.

This patent is subject to a terminal disclaimer.

(21) Appl. No.: 17/636,694

(22) PCT Filed: Aug. 18, 2020

(86) PCT No.: PCT/US2020/046795
§ 371 (c)(1),
(2) Date: Feb. 18, 2022

(87) PCT Pub. No.: WO2021/034822
PCT Pub. Date: Feb. 25, 2021

(65) Prior Publication Data
US 2022/0313272 A1   Oct. 6, 2022

Related U.S. Application Data

(63) Continuation-in-part of application No. 16/863,996, filed on Apr. 30, 2020, now Pat. No. 10,835,258.
(Continued)

(51) Int. Cl.
*A61B 17/12* (2006.01)
*A61B 17/00* (2006.01)
*A61B 90/00* (2016.01)

(52) U.S. Cl.
CPC .. *A61B 17/12136* (2013.01); *A61B 17/00234* (2013.01); *A61B 17/1204* (2013.01);
(Continued)

(58) Field of Classification Search
CPC .. A61M 25/10; A61M 1/3621; A61M 1/3613; A61B 17/1204; A61B 17/12136;
(Continued)

(56) References Cited

U.S. PATENT DOCUMENTS 5,011,468 A   4/1991  Lundquist et al.
5,258,042 A   11/1993 Mehta
(Continued)

FOREIGN PATENT DOCUMENTS

JP   4262733 B2   5/2009

OTHER PUBLICATIONS

Ricketts, H., "Side-Hole Balloon-Angioplasty Catheters," AJR, 144: (1985) p. 123-126, American Roentgen Ray Society, Leesburg, USA.
(Continued)

*Primary Examiner* — Tuan V Nguyen
(74) *Attorney, Agent, or Firm* — BLAIR WALKER IP SERVICES, LLC

(57) ABSTRACT

A method of providing retrograde perfusion of a patient's brain includes occluding a jugular vein of a subject at a jugular occlusion location, and passively shunting arterial blood from an artery of the subject to a location in the jugular vein distal to the jugular occlusion location.

18 Claims, 27 Drawing Sheets

Related U.S. Application Data

(60) Provisional application No. 62/889,968, filed on Aug. 21, 2019.

(52) U.S. Cl.
CPC ........ *A61B 17/12109* (2013.01); *A61B 90/37* (2016.02); *A61B 2017/00292* (2013.01); *A61B 2017/00539* (2013.01); *A61B 2090/376* (2016.02); *A61B 2090/378* (2016.02); *A61B 2576/026* (2013.01)

(58) Field of Classification Search
CPC ........ A61B 17/12109; A61B 17/00234; A61B 17/320725
See application file for complete search history.

(56) References Cited

U.S. PATENT DOCUMENTS

| | | |
|---|---|---|
| 5,374,239 A | 12/1994 | Mischenko |
| 5,794,629 A | 5/1998 | Frazee |
| 5,908,407 A | 6/1999 | Frazee et al. |
| 6,099,548 A | 8/2000 | Taheri |
| 6,110,139 A | 8/2000 | Loubser |
| 6,206,868 B1 | 3/2001 | Parodi |
| 6,386,202 B1 | 5/2002 | Frazee |
| 6,555,057 B1 | 4/2003 | Barbut et al. |
| 6,652,546 B1 | 11/2003 | Nash et al. |
| 6,723,116 B2 | 4/2004 | Taheri |
| 7,374,561 B2 | 5/2008 | Barbut |
| 8,157,760 B2 | 4/2012 | Criado et al. |
| 8,372,108 B2 | 2/2013 | Lashinski |
| 8,951,222 B2 | 2/2015 | Tarlian, Jr. et al. |
| 9,662,118 B2 | 5/2017 | Chang |
| 10,470,797 B1 | 11/2019 | Rai et al. |
| 2001/0038807 A1 | 11/2001 | Barbut et al. |
| 2002/0049402 A1 | 4/2002 | Peacock, III et al. |
| 2002/0082592 A1 | 6/2002 | Lary |
| 2002/0128586 A1 | 9/2002 | Barbut |
| 2002/0128679 A1 | 9/2002 | Turovskiy et al. |
| 2002/0151922 A1 | 10/2002 | Hogendijk et al. |
| 2003/0212304 A1 | 11/2003 | Lattouf |
| 2005/0137647 A1 | 6/2005 | Wallace et al. |
| 2008/0200946 A1 | 8/2008 | Braun et al. |
| 2009/0024072 A1* | 1/2009 | Criado ............ A61B 17/12109 604/9 |
| 2009/0198172 A1 | 8/2009 | Garrison et al. |
| 2011/0034986 A1 | 2/2011 | Chou et al. |
| 2012/0053614 A1 | 3/2012 | Mukherjee |
| 2012/0259244 A1 | 10/2012 | Roberts et al. |
| 2012/0302995 A1 | 11/2012 | Hochareon |
| 2013/0035628 A1 | 2/2013 | Garrison et al. |
| 2013/0281788 A1 | 10/2013 | Garrison et al. |
| 2015/0250500 A1 | 9/2015 | Dickinson et al. |
| 2016/0296690 A1 | 10/2016 | Kume et al. |
| 2018/0161551 A1 | 6/2018 | Pillai |
| 2020/0016381 A1 | 1/2020 | Calhoun et al. |
| 2020/0107838 A1 | 4/2020 | Pillai |
| 2020/0214716 A1 | 7/2020 | Pillai |

OTHER PUBLICATIONS

Frazee, J., Luo, X., Luan, G., Hinton, D., Hovda, D., Shiroishi, M., Barcliff, L., "Retrograde Transvenous Neuroperfusion: A Back Door Treatment for Stroke," Stroke, 29: (1998) p. 1912-1916, Lippincott Williams & Wilkins, Philadelphia, USA.

Kern, J., Arnold, S., "Massive Cerebral Embolization: Successful Treatment With Retrograde Perfusion," Ann Thorac Surg, 69: (2000) p. 1266-1268, Elsevier, New York, USA.

Hussain, S., Svensson, L., "Surgical techniques in type A dissection," Ann Cardiothorac Surg, 5(3): (2016) p. 233-235, AME Publishing Company, Hong Kong SAR, China.

Tanaka, A., Estrera, A., "Simple retrograde cerebral perfusion is as good as complex antegrade cerebral perfusion for hemiarch replacement," Perspective on Cardiac Surgery, 4(3): (2018) (22 pages), AME Publishing Company, Hong Kong SAR, China.

"Medtronic—Neurovascular 2017 Product List, Cello balloon guide catheters," http://docplayer.net/47807774-Neurovascular-2017-product-list-table-of-contents.html Available online as early as Jan. 10, 2020.

"Sniper—balloon occlusion microcatheter," https://embolx.com/ Available online as early as Dec. 16, 2019.

"Embolx Sniper," https://embolx.com/products/ Available online as early as Apr. 29, 2020.

"Retrograde Cerebral Perfusion" https://www.slideshare.net/dickyawartono/complex-aortic-arch-surgery Available online as early as Jan. 10, 2020.

Cleveland Clinic; Cerebral protection in TAVR: approval marks start of new era (3 pages) https://consultqd.clevelandclinic.org/cerebral-protection-in-tavr-approval-marks-start-of-a-new-era/ Available on the internet as early as Jan. 9, 2019.

Kwolek et al.; Results of the roadster multicenter trial of transcarotid stenting with dynamic flow reversal; Journal of Vascular Surgery; vol. 62, No. 5; pp. 1227-1234; Nov. 2015.

Medtronic; Mo Ma Ultra proximal cerebral protection device (4 pages) https://www.medtronic.com/us-en/healthcare-professionals/products/cardiovascular/embolic-protection-devices/mo-ma.html Available on the internet as early as Jan. 9, 2019.

Parodi et al.; Proximal occlusion and flow reversal: The ideal cerebral protection method during carotid artery stenting; Endovascular Today; pp. 67-71 (4 pages) https://evtoday.com/articles/2006-nov/EVT1106_07-php Available on the internet as early as Jan. 9, 2019.

Silkroad Medical; Enroute: Transcarotid neuroprotection and stent system (3 pages) https://silkroadmed.com/enroute-transcarotid-neuroprotection-system/ Available on the internet as early as Jan. 9, 2019.

Weber et al.; Proximal protection devices and flow reversal for embolic protection; Vascular Disease Management; pp. E21-E26 (9 pages); vol. 11, No. 1; Jan. 2014.

PCT International Search Report and Written Opinion for PCT/US2020/046795, Pillai, Lakshmikumar, Forms PCT/ISA/220, 210, and 237 dated Nov. 18, 2020 (7 pages).

Frazee, J., Jordan, S., Dion, J., Kar, S., Vinuela, F., Rand, R., Corday, E., "Ischemic Brain Rescue by Transvenous Perfusion in Baboons With Venous Sinus Occlusion," Stroke, 21: (1990) p. 87-93, Lippincott Williams & Wilkins, Philadelphia, USA.

Estrera A., Safi H., "Repair of the Transverse Arch Using Retrograde Cerebral Perfusion During Acute Type A Aortic Dissection," Cardiac Surgery, 10(1): (Mar. 1, 2005) pp. P3-22, Elsevier, https://www.optechtcs.com/article/S1522-2942(05)00007-3/fulltext.

Griepp R., Griepp E., "Perfusion and Cannulation Strategies for Neurological Protection in Aortic Arch Surgery," Found on Youtube Dec. 12, 2021. https://www.youtube.com/watch?v=oXEl0OalSNg Listed as posted Oct. 29, 2015.

Griepp R., "Retrograde Cerebral Perfusion: Results of Laboratory Studies" single slide, from lecture circa 2013.

Juvonen T., Weisz D., Wolfe D., Zhang N., Bodian C., Mccullough J., Mezrow C., Griepp R., "Can Retrograde Perfusion Mitigate Cerebral Injury After Particulate Embolization? a Study in a Chronic Porcine Model," The Journal of Thoracic and Cardiovascular Surgery, 115(5): (1998) pp. 1142-1159, Mosby, Inc.

Ueda, Y., "A reappraisal of retrograde cerebral perfusion," Annals of cardiovascular surgery, 2(3): (May 2013) pp. 316-325, AME Publishing Company, www.annalsets.com.

Yerlioglu M., Wolfe D., Mezrow C., Weisz D., Midulla P., Zhang N., Shiang H., Bodian C., Griepp R., "The Effect of Retrograde Cerebral Perfusion After Particulate Embolization to the Brain," The Journal of Thoracic and Cardiovascular Surgery, 110(5): (1995) pp. 1470-1485, Mosby-Year Book, Inc.

Österberg K., Falkenberg M., Resch T., "Endovascular Technique for Arterial Shunting to Prevent Intraoperative Ischemia," European Journal of Vascular and Endovascular Surgery, 48(2): (Aug. 2014) pp. 126-130, European Society for Vascular Surgery.

Murukendiran G., Sreedhar R., Gadhinglajkar S., Jagasih A., Babu S., Pitchai S., "To the Editor: The Dampening Arterial Trace—A

(56) References Cited

OTHER PUBLICATIONS

Rare Complication of Pruitt F3 Carotid Shunt Migration During Carotid Endarterectomy," Journal of Cardiothoracic and Vascular Anesthesia, 35: 2021 p. 1909, https://doi.org/10.1053/j.jvca.2020.10.046.

* cited by examiner

SYSTEMS AND METHODS FOR RETROGRADE PERFUSION AND CLEARANCE OF EMBOLI

BACKGROUND OF THE INVENTION

Field of the Invention

The field of the invention generally relates to systems and methods for providing retrograde perfusion of the brain and systems and methods for providing cerebral flow reversal.

SUMMARY OF THE INVENTION

In a first embodiment of the present disclosure, a method of providing retrograde perfusion of a patient's brain includes occluding a jugular vein of a subject at a jugular occlusion location, and passively shunting arterial blood from an artery of the subject to a location in the jugular vein distal to the jugular occlusion location.

In another embodiment of the present disclosure, a venous occlusion sheath for providing retrograde perfusion of a patient's brain includes an elongate shaft having a proximal end and a distal end, the distal end configured for placement within a jugular vein of a subject, an expandable occluder carried on the shaft at or adjacent the distal end of the shaft, the occluder having a collapsed configuration and an expanded configuration, a relief lumen extending through the shaft and having a proximal end and a distal end, the proximal end configured to be hydraulically coupled to a first location in the arteries of the subject, the distal end comprising one or more openings in the side of the shaft, and a blood perfusion lumen extending through the shaft and having a proximal end and a distal end, the proximal end configured to be hydraulically coupled to a second location in the arteries of the subject, the distal end comprising an opening located distal to the expandable occluder, the blood perfusion lumen having a length between its proximal end and its distal end, the blood perfusion lumen one or more transverse dimensions along its length, at least the length and the one or more transverse dimensions of the blood perfusion lumen together providing an overall flow resistance of the blood perfusion lumen, the overall flow resistance causing a pressure head loss of less than 95 mm Hg when blood having a temperature of between about 35° C. and about 39° C. is allowed to pass through the blood perfusion lumen from its proximal end to its distal end with a mean pressure at the proximal end of the blood perfusion lumen of 110 mm Hg.

In yet another embodiment of the present disclosure, a system for providing retrograde perfusion of a patient's brain and flow reversal includes a venous occlusion sheath including an elongate shaft having a proximal end and a distal end, the distal end configured for placement within a jugular vein of a subject, an expandable vein occluder carried on the shaft at or adjacent the distal end of the shaft, the expandable vein occluder having a collapsed configuration and an expanded configuration, a relief lumen extending through the shaft and having a proximal end and a distal end, the proximal end comprising a first connector, the distal end comprising one or more openings in the side of the shaft, and a blood perfusion lumen extending through the shaft and having a proximal end and a distal end, the proximal end comprising a second connector, the distal end comprising an opening located distal to the expandable vein occluder, an arterial occlusion sheath including an elongate shaft having a proximal end and a distal end, the distal end configured for placement within a carotid artery of a subject, an expandable artery occluder carried on the shaft at or adjacent the distal end of the shaft, the expandable artery occluder having a collapsed configuration and an expanded configuration, and a blood perfusion lumen extending through the shaft and having a proximal end and a distal end, the proximal end comprising a third connector, the distal end comprising an opening located distal to the expandable occluder, and wherein the first connector is configured to be hydraulically coupled to the third connector, and wherein the second connector is configured to be coupled to an arterial sheath.

DETAILED DESCRIPTION OF THE ILLUSTRATED EMBODIMENTS

The present disclosure relates to systems and methods for providing retrograde perfusion of the brain for feeding brain tissue. The present disclosure also related to systems and methods for causing flow reversal in the blood vessels of head and neck or for flushing out emboli from arteries. These emboli may include thromboemboli. The procedures described herein can be performed with an added external pump to aid perfusion by increasing the pressure gradient. However, the procedures described herein may also be performed without any use of an external pump, relying only on inherent blood pressure gradients to passively shunt blood from one area to another. Veins can be utilized to deliver oxygenated blood from arteries in the same patient. In addition, select occlusion of a vein and of an artery can together be used to cause flow reversal.

Interventional procedures in the carotid arteries are performed for a number of different reasons. Carotid stenting can be performed by an interventionist as an endovascular alternative to carotid endarterectomy. During the procedure, a stent is delivered via a catheter to a diseased portion of the carotid artery and expanded over the diseased portion to increase the luminal cross-sectional area of the artery. The diseased portion is often in the left or right internal carotid artery, just distal to where the common carotid artery bifurcates into the external carotid artery and the internal carotid artery. Because the internal carotid artery is a conduit delivering blood to brain tissue, emboli which may break off from the diseased portion during the expansion of the stent is at risk of being carried downstream and causing embolic or thromboembolic stroke. Distal protection devices are devices that are configured to protect areas downstream of the stent, by catching significant emboli that may be released. Some distal protection devices comprise baskets or filters, and are capable of retrieving and removing the emboli from the patient. Other devices have been developed to reverse the flow of blood in the carotid artery such that that emboli will not travel distally to the vessels feeding the brain tissue. In some systems, the flow is reversed and delivered into a vein, such as the jugular vein, so that the emboli are sent to the right side of the heart to be sent to the lungs, which are capable of serving as a filter of emboli of a certain size.

Figure 1:
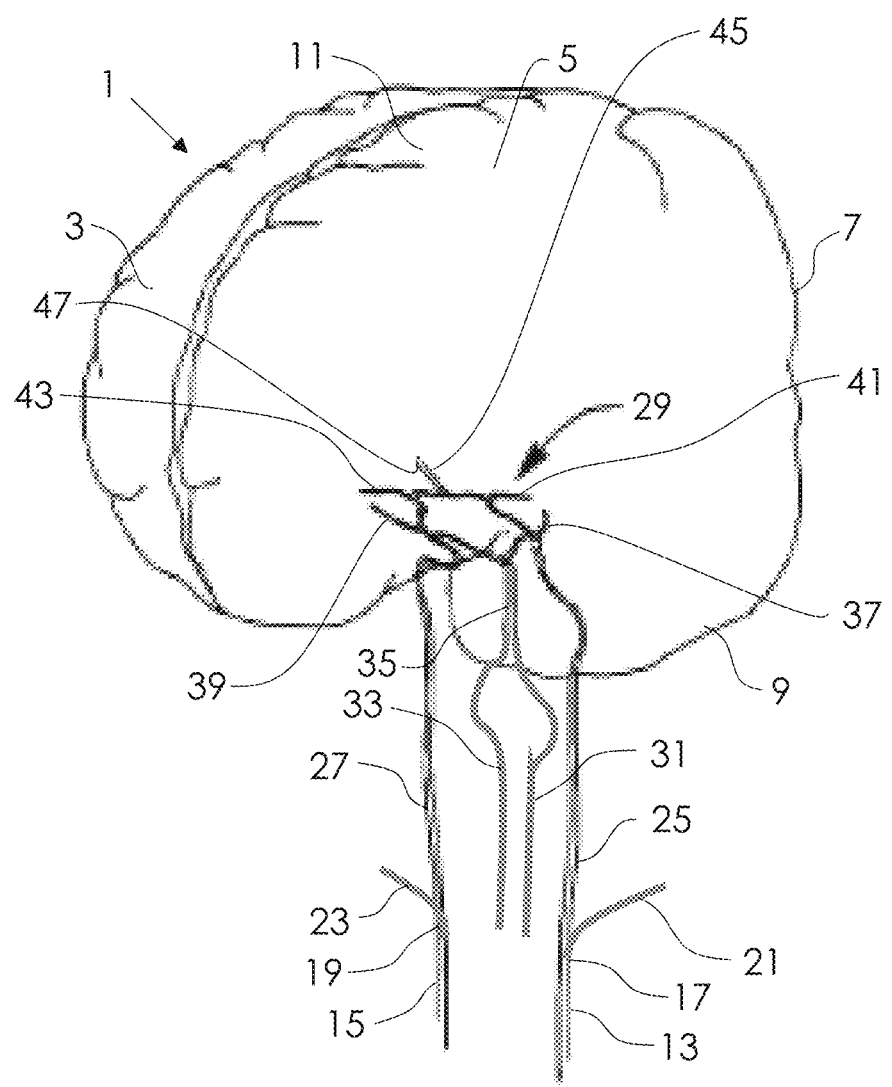
FIG. 1 is a perspective view of the arterial system feeding a human brain.

Other interventional procedures may be performed in the carotid artery or in other arteries of the head and neck. FIG. 1 illustrates a brain 1 having a cerebrum 11 having a frontal lobe 3, a parietal lobe 5, and an occipital lobe 7, and a cerebellum 9. Oxygenated blood from the lungs is pumped by the left side of the heart to the brain by two different routes, the carotid arteries and the vertebral arteries. The left common carotid 13 and right common carotid 15 arteries branch at bifurcations 17, 19 into left 21 and right 23 external carotid arteries and left 25 and right 27 internal carotid arteries. The internal carotid arteries 25, 27 form anastomoses with the Circle of Willis 29. The left 31 and right 33 vertebral arteries converse at the basilar artery 35, which then forms another anastomosis with the Circle of Willis 29. Cerebral thrombus may be found in a number of the vessels of the Circle of Willis 29, and may be the cause of thromboembolic stroke, the most common type of stroke (see thrombus 113 in FIG. 13). The cerebral arteries include the left 37 and right 39 posterior cerebral arteries (PCA), the left 41 and right 43 middle cerebral arteries (MCA), and the left 45 and right 47 anterior cerebral arteries (ACA). There are also other connecting arteries within the Circle of Willis. During thromboembolic stroke, a thrombus forms in a cerebral artery, or a previously formed thrombus migrates to a cerebral artery, causing ischemia and often occlusion of the particular vessel. Interventional devices, such as snares or aspiration catheters, can be used to remove some or all of the thrombus associated with thromboembolic stroke. During interventional procedures for thromboembolic or ischemic stroke, a patient is commonly given systemic heparin, and may also receive injections of tPA (tissue plasminogen activator) to attempt to break down the thrombus.

Another type of stroke, known as hemorrhagic stroke, involves rupture and bleeding of an aneurysm associated with one or more of the cerebral arteries, or the bleeding of other structures, such as an arteriovenous malformation (AVM). Hemorrhagic stroke may be treated in a number of different manners. Embolic materials may be implanted within a ruptured aneurysm or AVM in order to initiate occlusion and isolation of this feature. These materials may also be delivered into these features even if they have not yet ruptured, in order to prevent rupture from occurring. All of these procedures may have a potential of causing a thromboembolus to form, for example, on the catheter, and the risk that the thromboembolus breaks off and travels downstream to occlude one or more artery, and cause thromboembolic stroke. Additionally, interventional devices may cause other materials such as atherosclerotic plaque to break off and travel downstream, potentially causing embolic stroke. The embolic materials used in the treatment of aneurysms or AVMs may break off or migrate into the native arteries and travel to unwanted areas, also causing potential embolic stroke. Finally, the interventional devices themselves may fracture, sending one or more embolus distally in the circulation, as another potential nidus for embolic stroke.

Whether an interventionist is performing a carotid stenting procedure, a thrombus removal procedure, an embolization procedure, or any other procedure in the carotids, the vertebral arteries or basilar artery, or the cerebral vessels, the risk of embolism or thromboembolism is potential complication that can be fatal to the patient. During an interventional procedure, the normal circulation may be temporarily slowed or blocked by an access catheter, such as a guiding catheter, a microcatheter, or a flow-directed catheter, and may cause temporary ischemia to brain tissue of the patient. The systems and methods for providing retrograde perfusion of the brain disclosed herein are in some embodiments configured to provide perfusion of brain tissue that would otherwise be compromised. In some embodiments, the systems and methods for providing retrograde perfusion of the brain are configured to actively flush emboli, including thromboemboli, or other emboli, out of arteries or features in the Circle of Willis and sent proximally where they can be snared, retrieved, diminished, or diverted.

Figure 2:
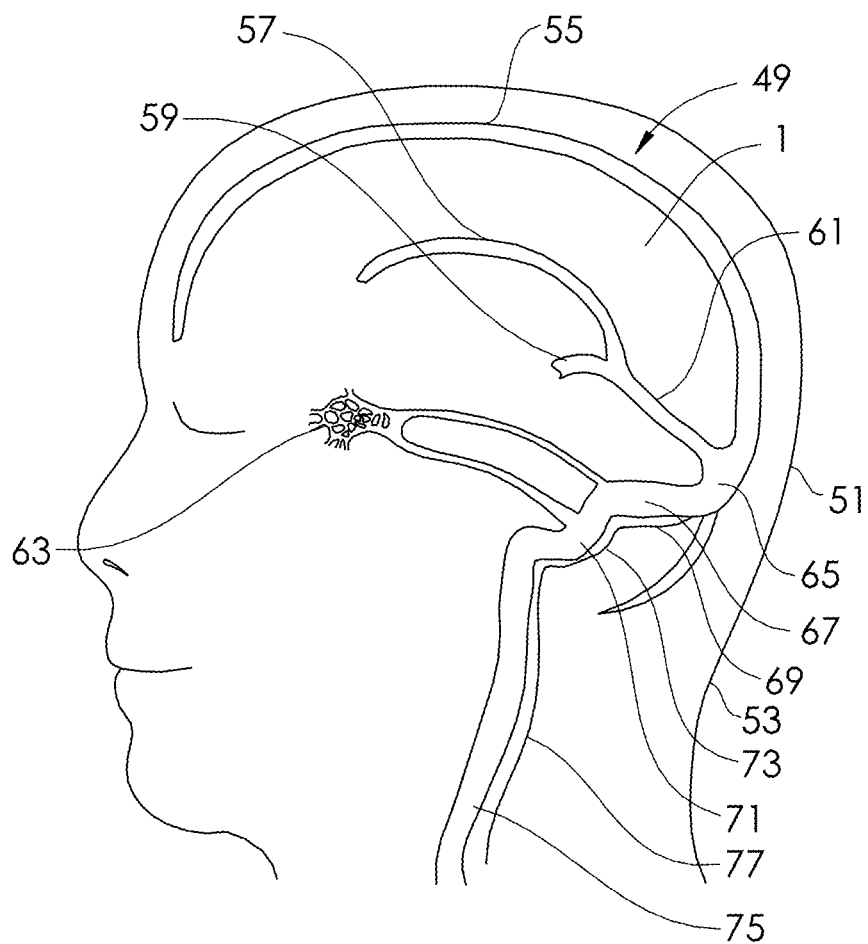
FIG. 2 is a side view of the main venous system of the human brain.

FIG. 2 illustrates the venous system 49 of the brain 1 of the head 51 a human 53, configured for draining the blood from the brain tissue and returning it to the heart for re-oxygenation and re-circulation. Multiple cerebral veins (not shown) anastomose to and feed the superior sagittal sinus 55, the inferior sagittal sinus 57 and the great cerebral vein 59. The inferior sagittal sinus 57 and the great cerebral vein 59 converge to the straight sinus 61, which communicates with a bifurcation 65 to the left transverse sinus 67 and the right transverse sinus 69. The cavernous sinus 63 also communicates to the left and right sigmoid sinuses 71, 73, which then communicate to the left internal jugular vein 75 and the right internal jugular vein 77. A vertebral vein system (not shown) also exists.

Figure 3:
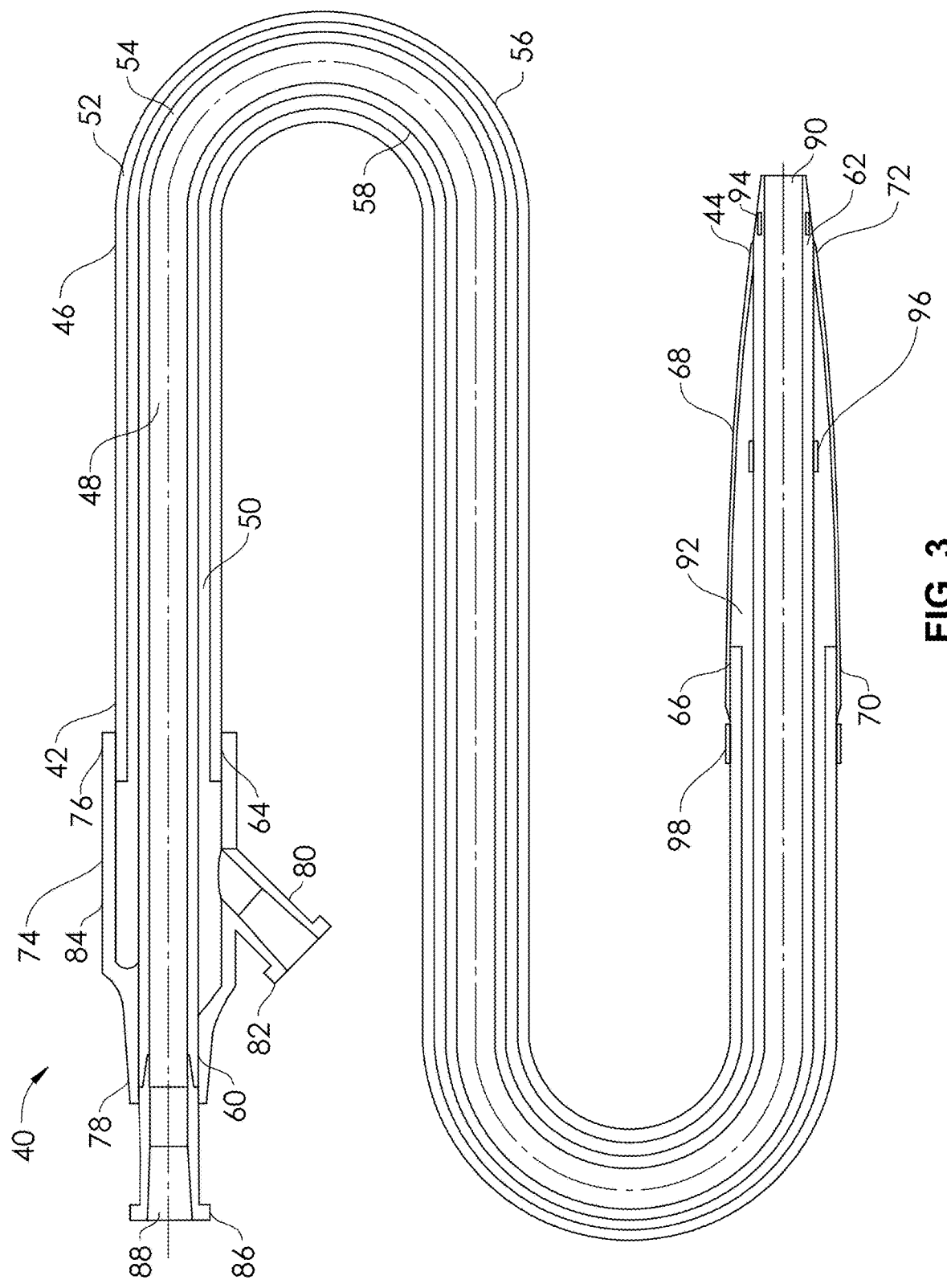
FIG. 3 is a sectional view of an occluding perfusion catheter according to an embodiment of the present disclosure.
Figure 4:
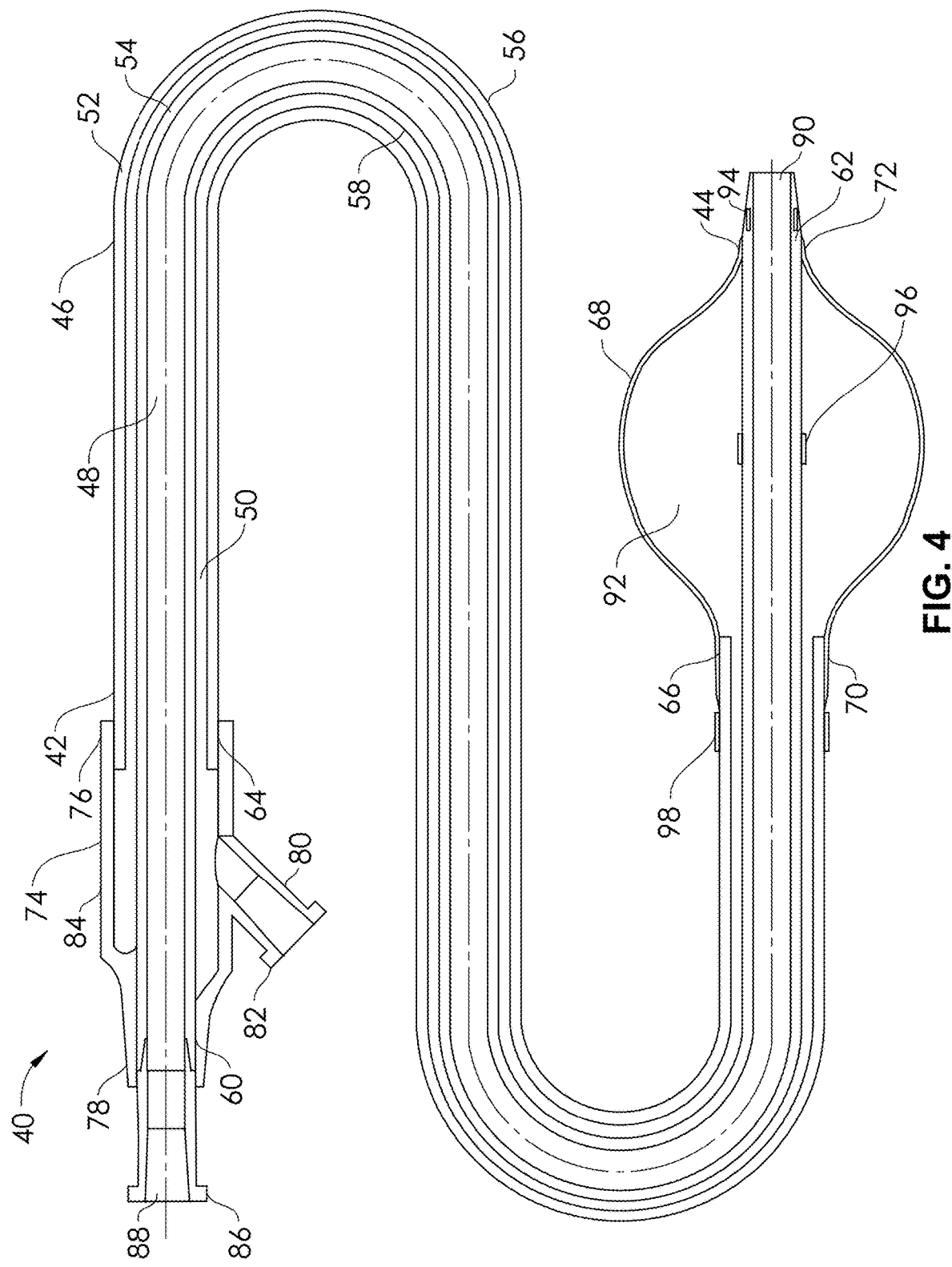
FIG. 4 is a sectional view of the occluding perfusion catheter of FIG. 3, with the balloon inflated.

FIGS. 3-4 illustrate an occluding perfusion catheter 40 having a proximal end 42 and a distal end 44. The occluding perfusion catheter 40 comprises a shaft 46 having a thru lumen 48 and an inflation lumen 50. In some embodiments, the thru lumen 48 and inflation lumen 50 may be arrayed side-by-side in the shaft 46, for example, with each lumen having a D-shapes cross-section, or with one lumen having a circular cross section and the other lumen having a crescent-shaped cross-section. However, in the embodiment illustrated in FIGS. 3-4, the thru lumen 48 has a circular cross-section and the inflation lumen 50 has an annular cross-section, extending around the thru lumen 48. The inflation lumen 50 is contained between an annular outer wall 52 of the shaft 46 and an annular inner wall 54 of the shaft 46. In some embodiments, the outer wall 52 defines an outer tube 56 and the inner wall 54 defines an inner tube 58, inserted within the outer tube 56. The inner tube 58 includes a proximal end 60 and a distal end 62, and the outer tube 56 includes a proximal end 64 and a distal end 66. An occlusion balloon 68 comprises a proximal end 70 sealingly bonded to the distal end 66 of the outer tube 56 and a distal end 72 sealingly bonded to the distal end 62 of the inner tube 58. The proximal end 70 and distal end 72 of the occlusion balloon 68 may be bonded with adhesive, and/or may be wound in place. The occlusion balloon 68 may comprise an elastomeric tube, comprising silicone, urethane, polyether block amide, or another thermoplastic elastomer. FIG. 3 illustrates the occlusion balloon 68 in its deflated state, and FIG. 4 illustrates the occlusion balloon 68 in its inflated state. The outer tube 56 and inner tube 58 may each comprise one or more of the following polymers: polyamide, polyurethane, polyether block amide, polyvinyl chloride, polyethylene, polypropylene, or other polyolefins. The occlusion balloon 68 may have an expanded diameter of between about 6 mm and about 14 mm, or between about 8 mm and about 12 mm.

A y-connector 74 is molded or otherwise formed from a rigid polymer such as polycarbonate, and has a distal end 76 that is sealingly bonded to the proximal end 64 of the outer tube 56 and a proximal end 78 that is sealingly bonded to the proximal end 60 of the inner tube 58. A side port 80 comprising a female luer connector 82 extends radially and proximally from a body 84 of the y-connector 74. A proximal female luer 86 is sealingly bonded to the proximal end 78 of the y-connector 74 and/or to the proximal end 60 of the inner tube 58. Thus, the thru lumen 48 extends between the tapered inlet 88 of the proximal female luer 86 to a distal opening 90 at the distal end 44 of the occluding perfusion catheter 40. The thru lumen 48 is configured for the placement of a guidewire (not shown in FIGS. 3-4), but is also configured for the passage of blood. For example, the blood may travel proximal to distal within the thru lumen 48. In some cases, the blood passes through the thru lumen 48 when the guidewire is removed from the thru lumen 48. In some cases, the blood passes through the thru lumen 48 with the guidewire still at least partially, or completely, in place within the thru lumen 48. Different guidewire sizes (outer diameters) may be used, such as 0.012 inch, 0.014 inch, 0.018 inch, 0.021 inch, 0.025 inch, 0.028 inch, 0.032 inch, 0.035 inch, or 0.038 inch. The female luer 82 of the side port 80 is configured for attaching a male luer connector of a syringe or an inflation device, such that inflation fluid such as saline, contrast media, or a mixture or the two, may be injected through the inflation lumen 50 to increase the volume of an interior 92 of the occlusion balloon 68, thus inflating it. The occlusion balloon 68 can be deflated by pulling a negative pressure or evacuating the syringe or inflation device (FIG. 3). One or more marker bands 94, 96, 98 may be carried on the occluding perfusion catheter 40 to allow visualization of the area of the occlusion balloon 68 and/or the distal end 44. The marker bands 94, 96, 98 may comprise radiopaque materials, such as platinum, tantalum, gold, or an alloy, such as 90% platinum and 10% iridium. A first marker band 94 is carried on the distal end 62 of the inner tube 58, and may be attached by adhesive or epoxy, or may be swaged, sputtered, heat bonded, or plated in place. A second marker band 96 is carried on the inner tube 58, and may be attached by adhesive or epoxy, or may be swaged, sputtered, heat bonded, or plated in place. A third marker band 98 is carried on the distal end 66 of the outer tube 56, and may be attached by adhesive or epoxy, or may be swaged, sputtered, heat bonded or plated in place. In some embodiments, only the second marker band 96 is necessary, as it demonstrates the location of the center of the occlusion balloon 68. In some embodiments, only the first marker band 94 and the third marker band 98 are necessary, as they demonstrate the general location of the ends of occlusion balloon 68. In some embodiments, only one of the marker bands 94, 98 may be used.

Figure 5:
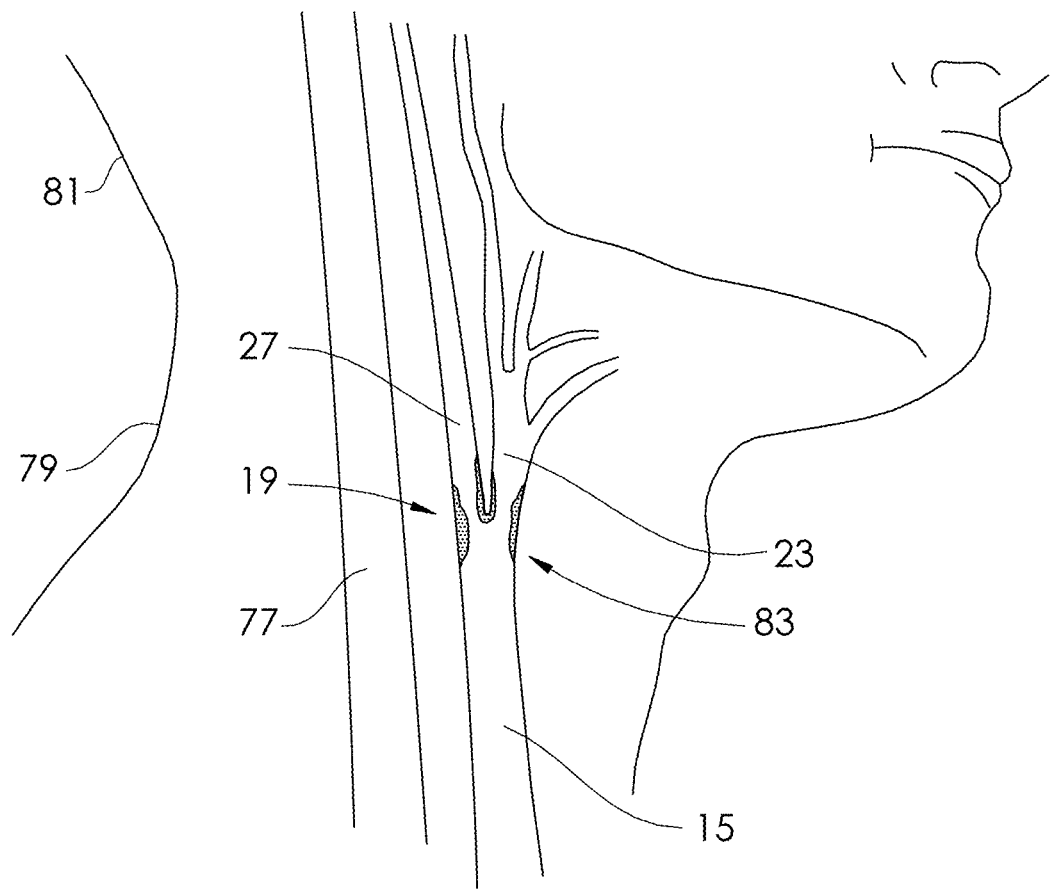
FIG. 5 is a side view of the vasculature in a patient's neck.

FIG. 5 illustrates relevant vasculature in the neck 79 of a patient 81. The right common carotid artery 15 branches at the bifurcation 19 into the right internal carotid artery 27 and the right external carotid artery 23. The right internal jugular vein 77 extends substantially parallel. Plaque 83 may be located, as shown, on any one, some, or all of: the common carotid artery 15, the internal carotid artery 27, and the external carotid artery 23. Thus, the plaque 83 may be located at anyone, some or all of the following locations: distal to the bifurcation 19, at the bifurcation 19, or proximal to the bifurcation 19. For consistency, the word "distal" is used herein, when referring to either veins or arteries, as a more branched portion, or a portion further away from the central vessels. The word "proximal," when referring to either veins or arteries, is used in the opposite manner. Thus, an internal jugular vein is distal to the superior vena cava, and an internal carotid artery is distal to the aorta. Likewise, the superior vena cava is proximal to the internal jugular veins, and the aorta is proximal to the internal carotid arteries. The words "proximal" and "distal" are used herein, when referring to catheters and other elongate medical devices, in the standard manner. The proximal end of the device is the end near the attending physician or medical personnel, and the distal end of the device is the portion inserted into the body of the patient.

Figure 6:
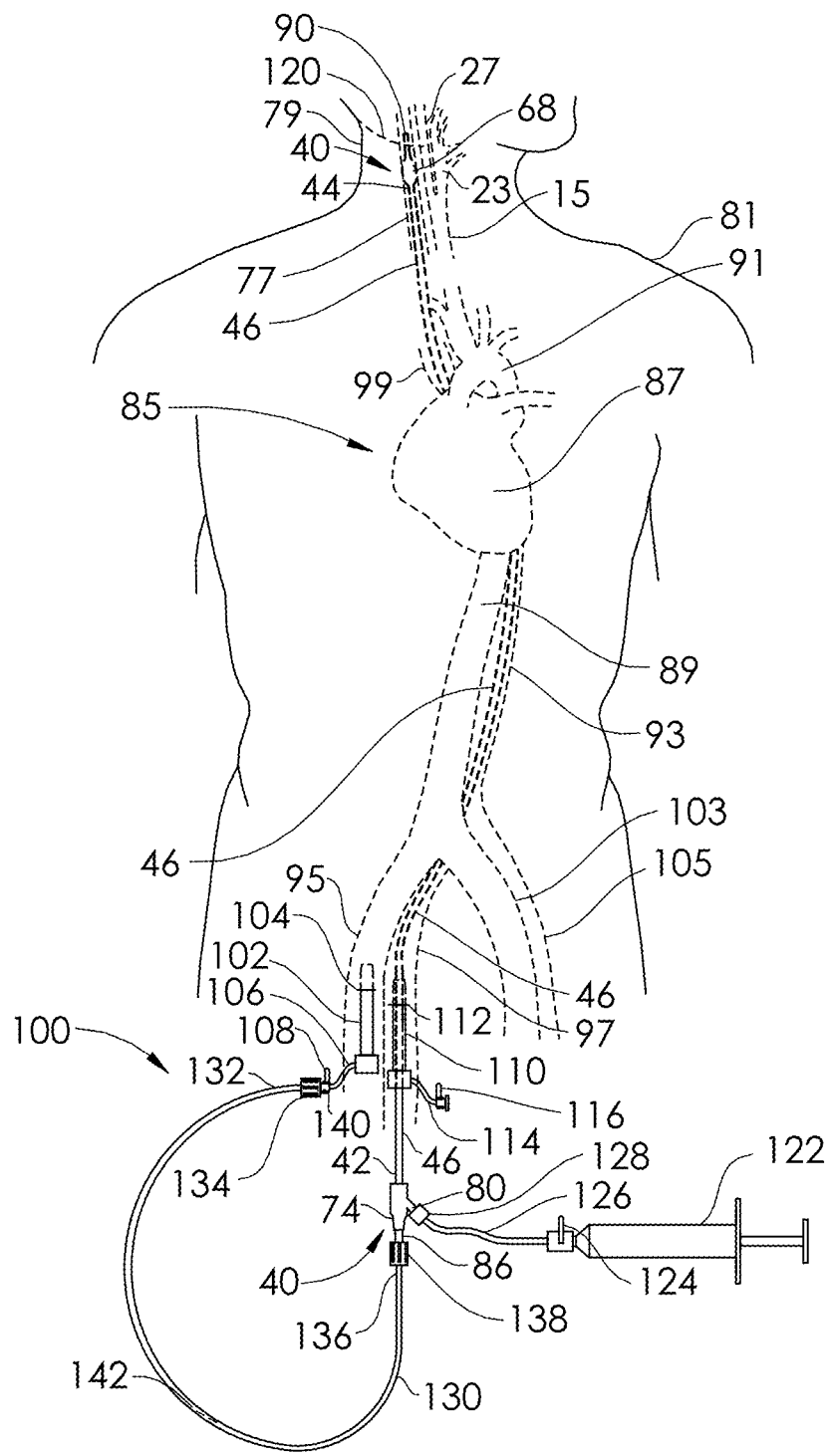
FIG. 6 is a view of an occluding perfusion system in place within a patient's vasculature, according to an embodiment in the present disclosure.
Figure 7:
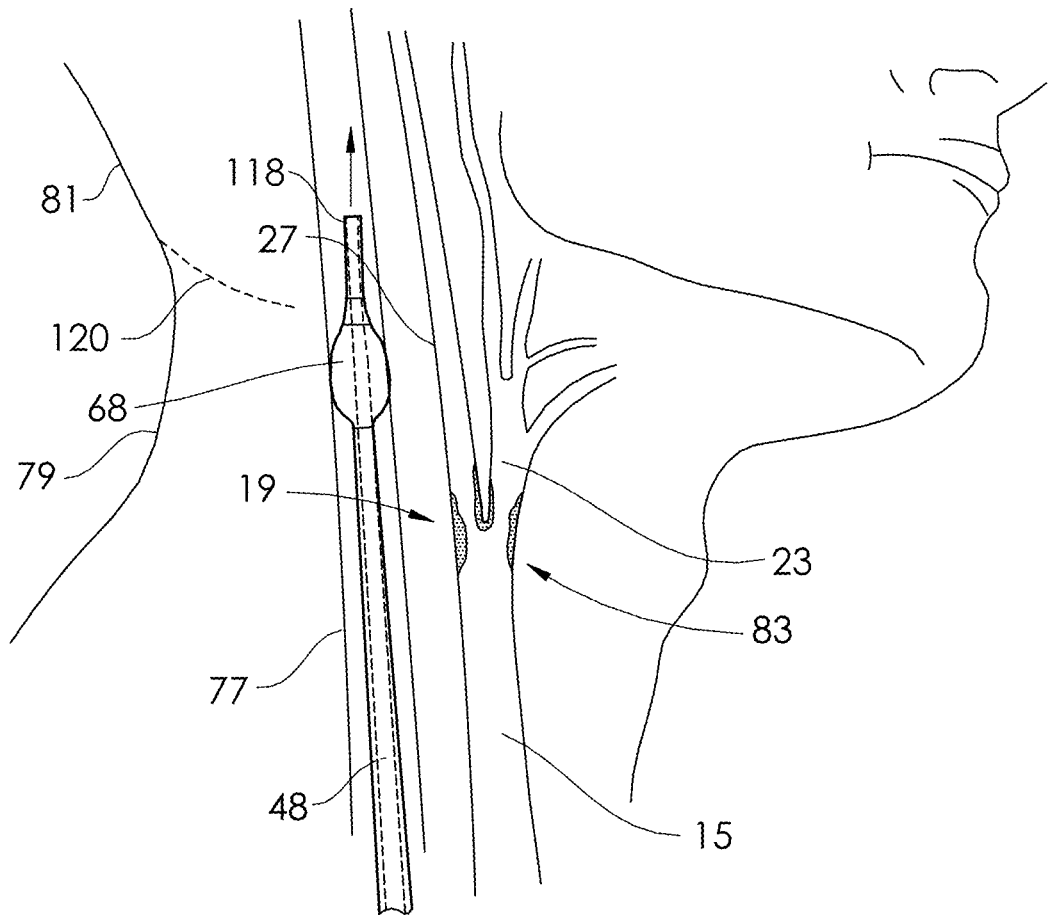
FIG. 7 is a detail view of the distal end of the occluding perfusion catheter of the occluding perfusion system of FIG. 6.
Figure 8:
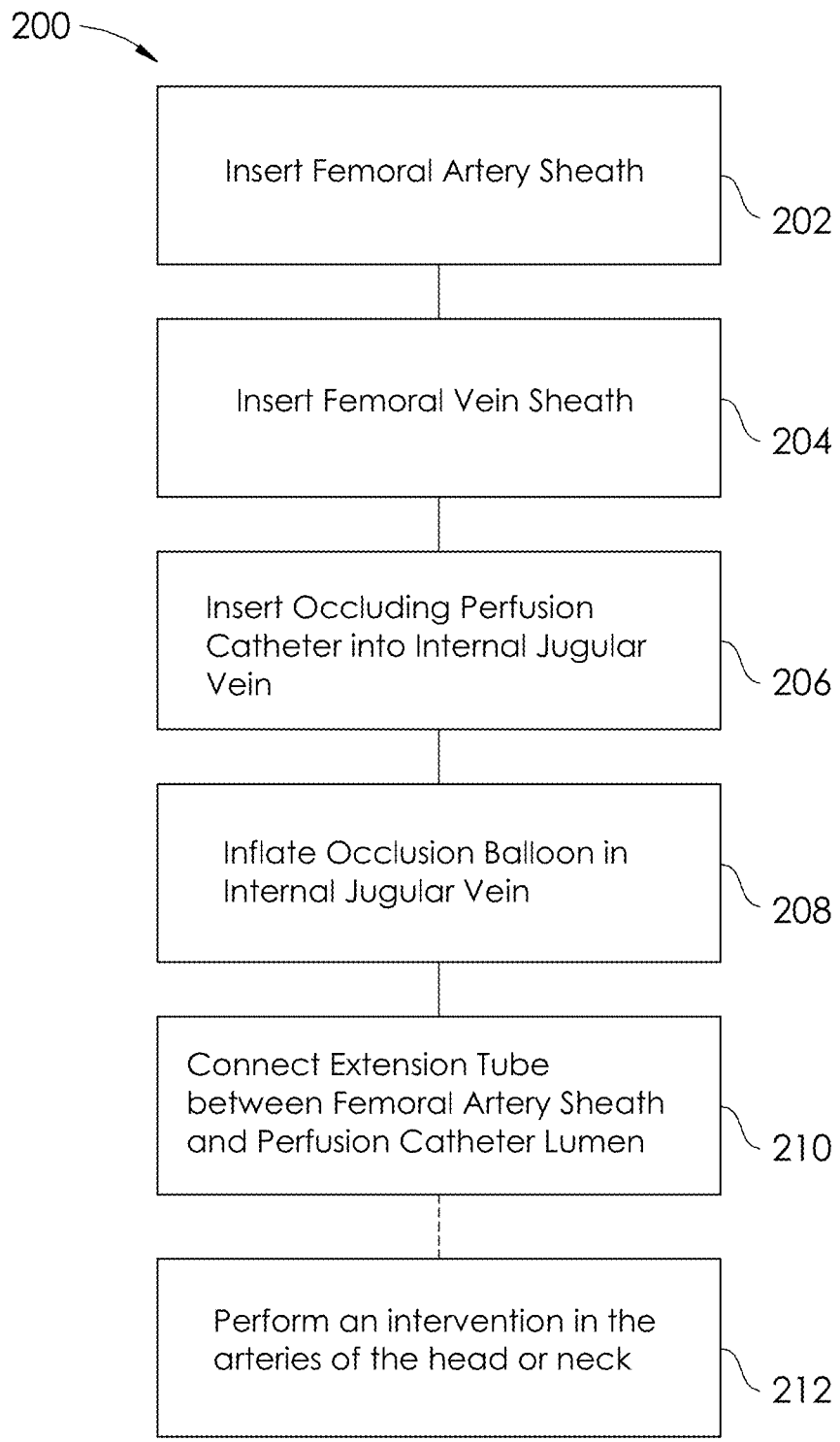
FIG. 8 is a block diagram of a method for performing retrograde perfusion of a patient's brain using the occluding perfusion system of FIG. 6, according to an embodiment of the present disclosure.

FIG. 6 illustrates an occluding perfusion system 100 and the circulatory system 85 of a patient 81, including the heart 87, aorta 89, aortic arch 91, inferior vena cava 93, superior vena cava 99, right femoral artery 95, and right femoral vein 97. The occluding perfusion system 100 comprises an occluding perfusion catheter 40 (FIGS. 6-7), similar to the occluding perfusion catheter 40 of FIGS. 3 and 4, and is used in accordance with a method 200 for performing retrograde perfusion of the brain, as diagrammed in FIG. 8. In step 202, a user inserts an introducer sheath 102 into the right femoral artery 95 through a first insertion site 104 (e.g. puncture), using a percutaneous Seldinger technique. The introducer sheath 102 may comprise an 8 F (French size) short sheath, but may comprise other sizes (e.g., 6 F to 10 F, or 7 F to 9 F), or other lengths. The introducer sheath 102 includes a side port 106 having a stopcock 108. The stopcock 108 is shown in the closed position in FIG. 6. In step 204, the user inserts an introducer sheath 110 into the right femoral vein 97 through a second insertion site 112 (e.g. puncture), using a percutaneous Seldinger technique. The introducer sheath 110 may comprise a 10 F (French size) short sheath, but may comprise other sizes (e.g., 7 F to 12 F, or 9 F to 11 F), or other lengths. The introducer sheath 110 includes a side port 114 having a stopcock 116. The stopcock 116 is shown in the closed position in FIG. 6. In step 206, the user inserts the occluding perfusion catheter 40 through the venous-placed introducer sheath 110, and advances the distal end 44 of the occluding perfusion catheter 40 through the inferior vena cava 93, the right atrium (not shown) of the heart 87, the superior vena cava 99, the right brachiocephalic vein (not shown) and into an internal jugular vein, in the case of FIGS. 6-7, the right internal jugular vein 77. Alternatively, or additionally, the left femoral artery 103 may be used for placement of the arterial sheath 102, or to place a second arterial sheath. Alternatively, or additionally, the left femoral vein 105 may be used for placement of the venous introducer sheath 110. In some catheter, the venous introducer sheath 110 may be avoided, skipping step 204, and the occluding perfusion catheter 40 may be inserted directly through the second insertion site 112. Either way, the occluding perfusion catheter 40 may comprise a size of between 7 F and about 12 F, or between 8 F and 10 F. The distal end 44 of the occluding perfusion catheter 40 includes an atraumatic distal tip 118 (FIG. 7). In step 206, the occluding perfusion catheter 40 is advanced by the user such that the distal tip 118 is located approximately at the skull base 120.

Figure 9:
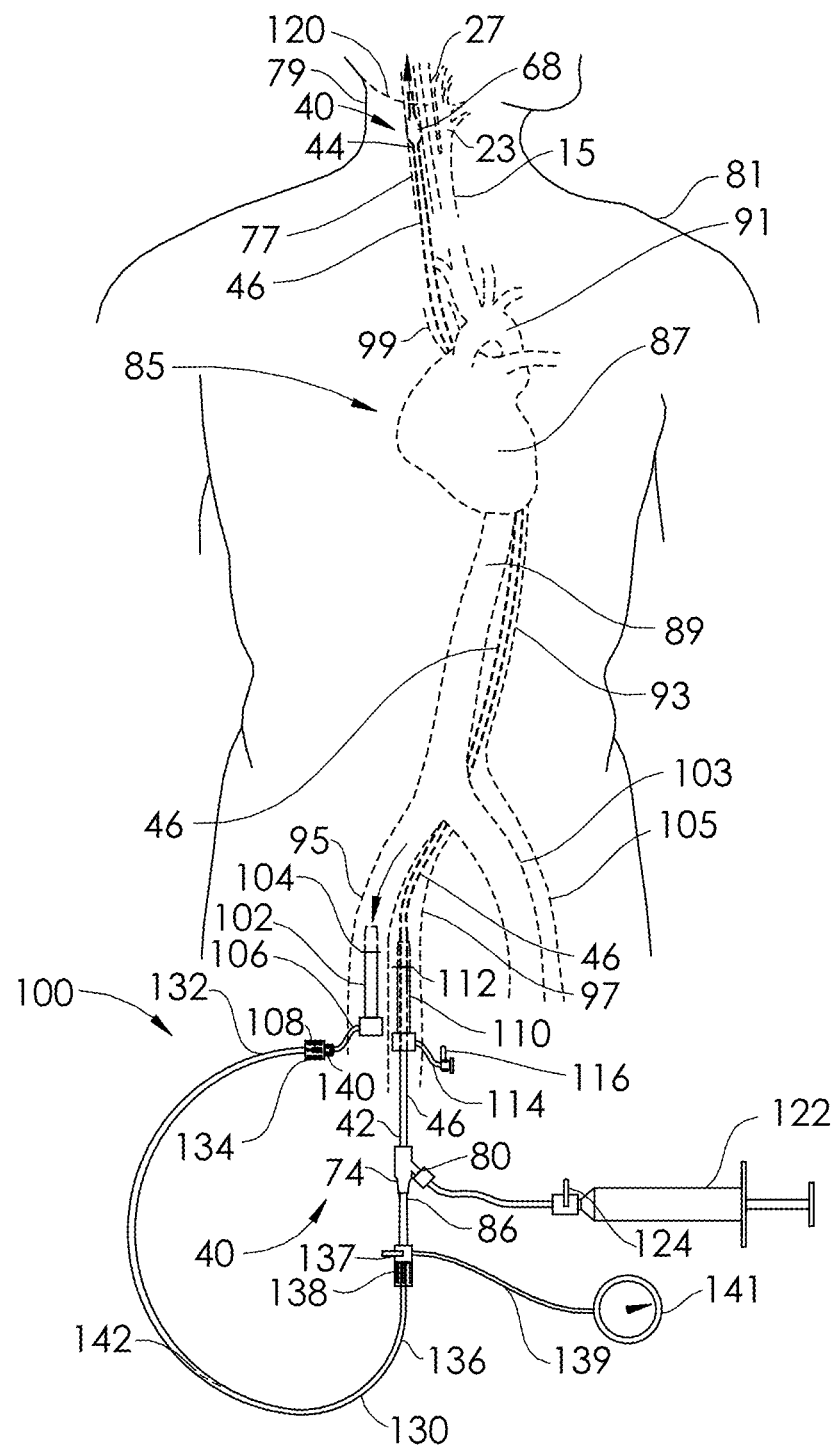
FIG. 9 is a view of an occluding perfusion system in operation within a patient's vasculature, according to an embodiment in the present disclosure.

In step 208, the user inflates the occlusion balloon 68 of the occluding perfusion catheter 40 with a syringe 122 or other inflation device, such that the occlusion balloon 68 occludes the right internal jugular vein 77. A stopcock 124 attached to the syringe 122 may then be closed, as shown in FIG. 6, to hold the desired balloon inflation volume or balloon inflation pressure. An extension tube 126 having a male luer 128 is shown in FIG. 6 with the male luer coupled to the side port 80 of the y-connector of the occluding perfusion catheter 40. The extension tube 126 is shown in FIG. 6 extending between the stopcock 124 and side port 80 but alternatively, the stopcock 124 may be located at the male luer, 128, or may be a separate component that is attachable to the male luer 128 and to the side port 80. In step 210, the user attaches an extension tube 130 between the arterial introducer sheath 102 and the occluding perfusion catheter 40. The extension tube 130 has a first end 132 having a first male luer 134 and a second end 136 having a second male luer 138. The first male luer 136 is coupled to a female luer 140 at the side port 106 of the introducer sheath 102 and the stopcock 108 is opened, allowing arterial blood to flow from the right iliac artery (or inferior vena cava, if the sheath 102 is not a short sheath) so that the blood fills the lumen 142 of the extension tube 130 of to the end of the second male luer 138. The second male luer 138 is then attached to the proximal female luer 86 of the y-connector 74 of the occluding perfusion catheter 40. Arterial blood from the right iliac artery is now passively shunted through the thru lumen 48 occluding perfusion catheter 40 and retrogradely through the right internal jugular vein 77, thus feeding tissue of the brain 1 with oxygenated blood. As there are typically no valves in the internal jugular vein above the internal jugular valve (which is typically below the skull base) there are no physical barriers to stop the shunted flow. Thus, the reverse flow (straight arrow, FIG. 7) is successfully achieved in a passive manner, from the connection of the extension tube 130 alone, because the arterial pressure at the distal tip of the sheath 102 is in most situations significantly greater than the typical venous pressure at the distal tip 118 of the occluding perfusion catheter 40, at its location within the right internal jugular vein 77. The word "passive" as used herein is intended to mean without the aid of a pump. FIG. 9 illustrates the occluding perfusion system 100 during retrograde perfusion of the brain 1. The stopcock 108 is in the open position.

Figure 10:
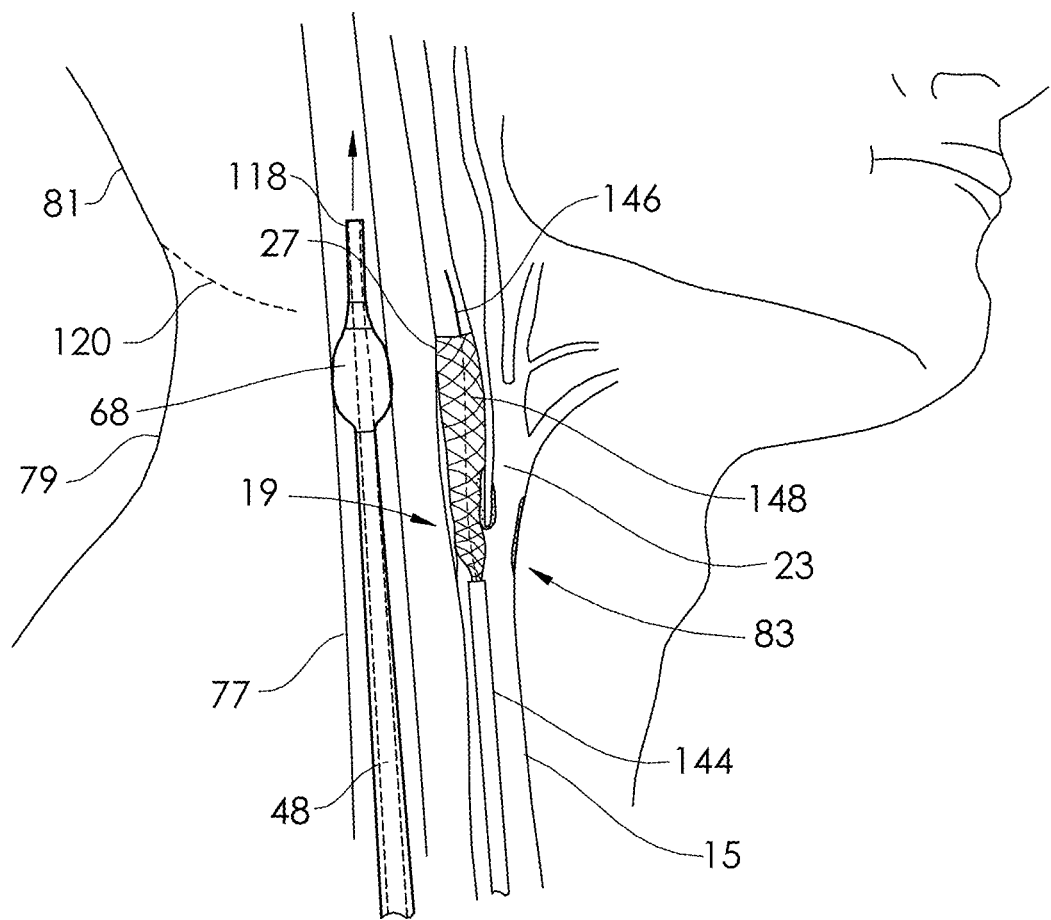
FIG. 10 is a detail view of the occluding perfusion system of FIG. 9 in operation during a stenting procedure.

FIG. 10 illustrates the occluding perfusion system 100 performing retrograde perfusion of the brain 1 during a carotid stenting procedure. A stent delivery catheter 144 is tracked over a guidewire 146 through the right common carotid artery 15 and the right internal carotid artery 27, and the catheter 144 is pulled back, to expand a self-expandable stent 148 within the diseased portion of the right internal carotid artery 27, and within some of the right common carotid artery 15. Other types of stent delivery may be used, such as the delivery of balloon expandable stents. By utilizing retrograde perfusion of brain tissue during the stenting procedure, the brain is protected during any portions of the procedure in which the right internal carotid artery 27 is significantly occluded or has its flow interrupted. In some cases, this may provide the user enough confidence to avoid the use of distal carotid occlusion, distal protection devices, or distal temporary filters during certain procedures.

Although one or more of the femoral veins 97, 105 has been described as the puncture/entry site for the introducer sheath 110 and the occluding perfusion catheter 40 (or the occluding perfusion catheter 40 without the introducer sheath 110), alternatively other veins may be utilized. For example, the left or right internal jugular vein, brachial vein, subclavian vein, axillary vein, or radial vein may be utilized. Although one of the femoral arteries femoral arteries 95, 103 has been described as the puncture/entry site for the introducer sheath 102, alternatively other arteries may be utilized. For example, the left or right brachial artery, axillary artery, or radial artery may be utilized. Ultrasound imaging, radiography, or fluoroscopy may be used to locate the jugular vein.

Figure 11:
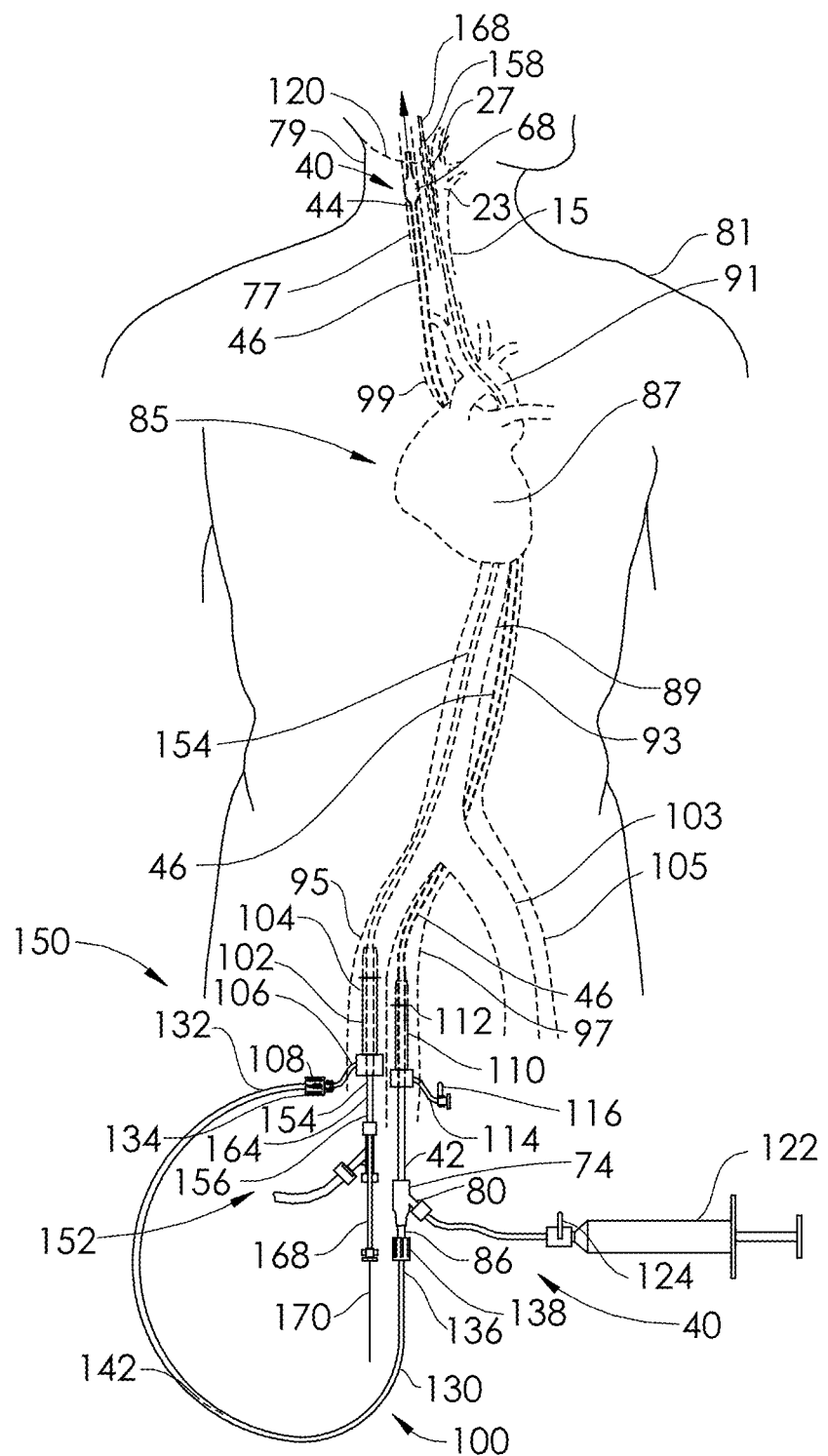
FIG. 11 is a view of a system for performing a cerebral intervention, according to an embodiment of the present disclosure.
Figure 12:
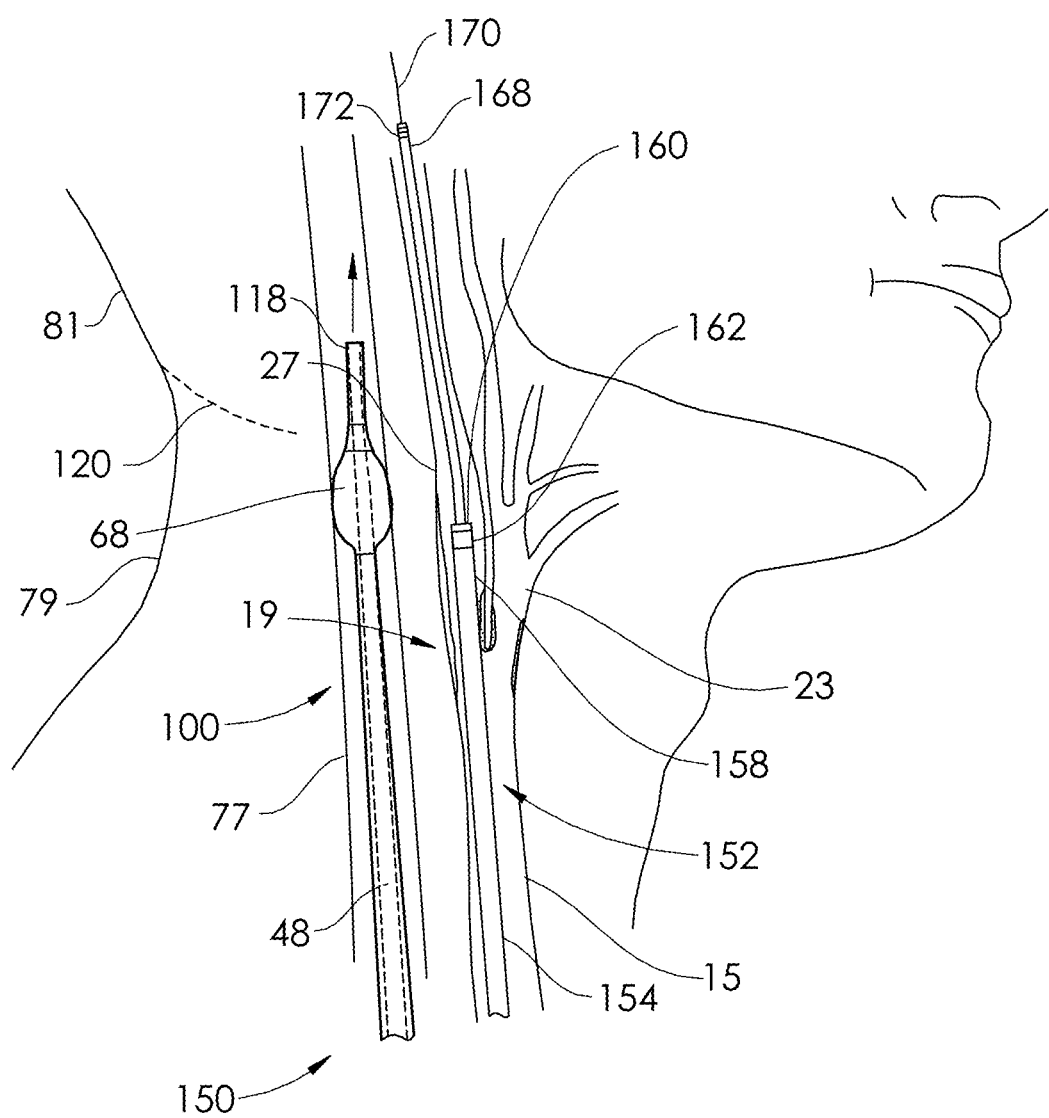
FIG. 12 is a detail view of the occlusion perfusion system of FIG. 11 in operation during a procedure involving the Circle of Willis.

FIG. 11 illustrates a system for performing a cerebral intervention 150 comprising the occluding perfusion system 100 and an arterial intervention system 152. The arterial intervention system 152 comprises a guiding catheter 154

Figure 13:
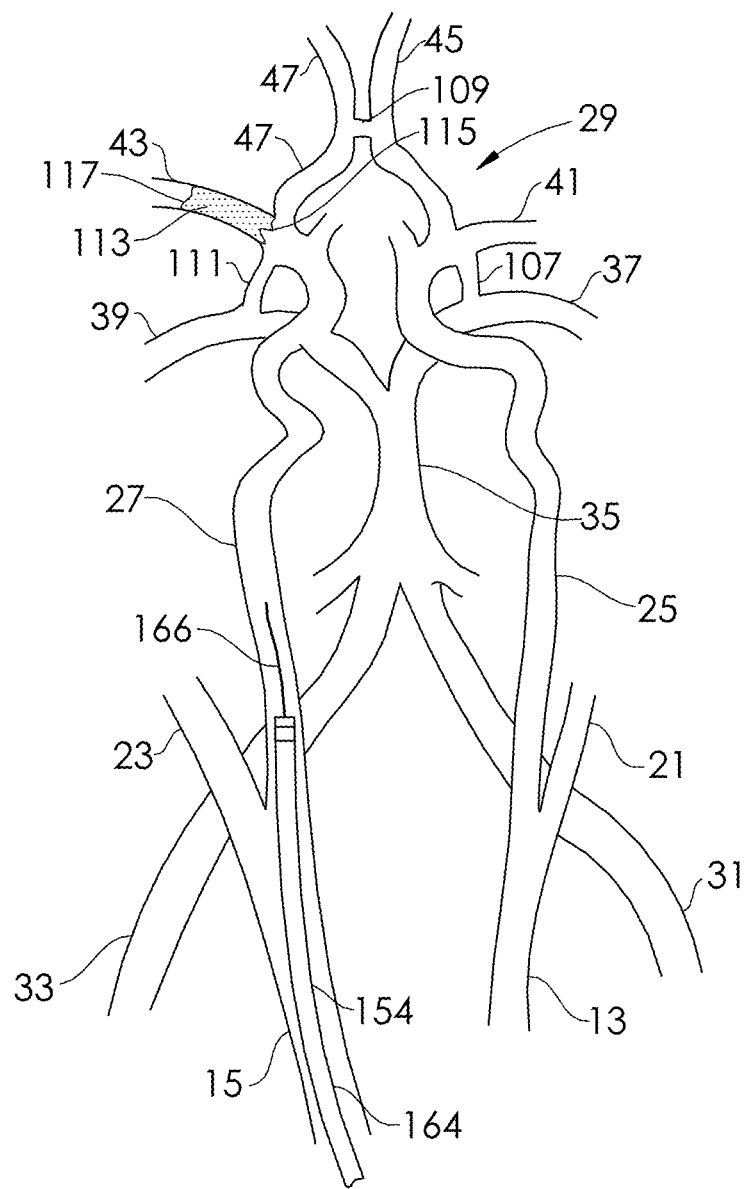
FIG. 13 is a detail view of a thrombus causing ischemic stroke in the Circle of Willis.

(or long sheath) having a proximal end 156 and a distal end 158, and a lumen 160 (FIG. 12) extending therebetween. The distal end 158 of the guiding catheter 154 includes a radiopaque marker band 162 comprising platinum or gold, but alternatively, or additionally, the guiding catheter 154 may comprise a shaft comprising polymeric materials having radiopaque additives, such as tantalum or titanium dioxide. A user follows the steps 202-210 of FIG. 8, and may choose a larger introducer sheath 102 to place in the right femoral artery 95, to allow the placement of the guiding catheter 154 through the lumen of the introducer sheath 102, and to also allow some space for arterial blood flow through the introducer sheath 102, around the shaft 164 of the guiding catheter 154. The user inserts the guiding catheter 154 through the introducer sheath 102 with a guidewire (e.g., 0.035 inch or 0.038 inch diameter) 166 (FIG. 13) inserted through the lumen 160 of the guiding catheter 154. Using the guidewire 166, the user advances the guiding catheter 154 through the aorta 89, and from the aortic arch 91, up into the right common carotid artery 15, and subselectively into the right internal carotid artery 27. FIG. 13 illustrates a thrombus 113 occluding the right middle cerebral artery 43 (MCA). This sort of occlusion may lead to ischemic stroke. The thrombus 113 has a proximal end 115 and a distal end 117. The left and right 41, 43 middle cerebral arteries communicate with the left and right posterior cerebral arteries 37, 39, respectively, via the left and right posterior communicating arteries 107, 111. The anterior communicating artery 109 is a communication between the left and right anterior cerebral arteries 45, 47. Returning to FIGS. 11-12, the user removes the guidewire 166, and places an interventional catheter 168 through the lumen 160 of the guiding catheter 154, tracking the interventional catheter 168 deeper into the right internal carotid artery 27, an into the vessels of the Circle of Willis 29, where the intervention is to be performed. The interventional catheter 168 may be delivered over a guidewire 170, such as a 0.012 inch or a 0.014 inch guidewire, and may have a radiopaque marker band 172. Alternatively, the interventional catheter may be flow-directed, and not require a guidewire 170. Step 212 is an additional step to the method 200 of FIG. 8 that comprises generally performing an intervention in the arteries of the head or neck. The intervention may comprise an intervention in a carotid artery, as shown in FIG. 10, or may comprise performing a cerebral intervention, as shown in FIGS. 11-15.

Figure 14:
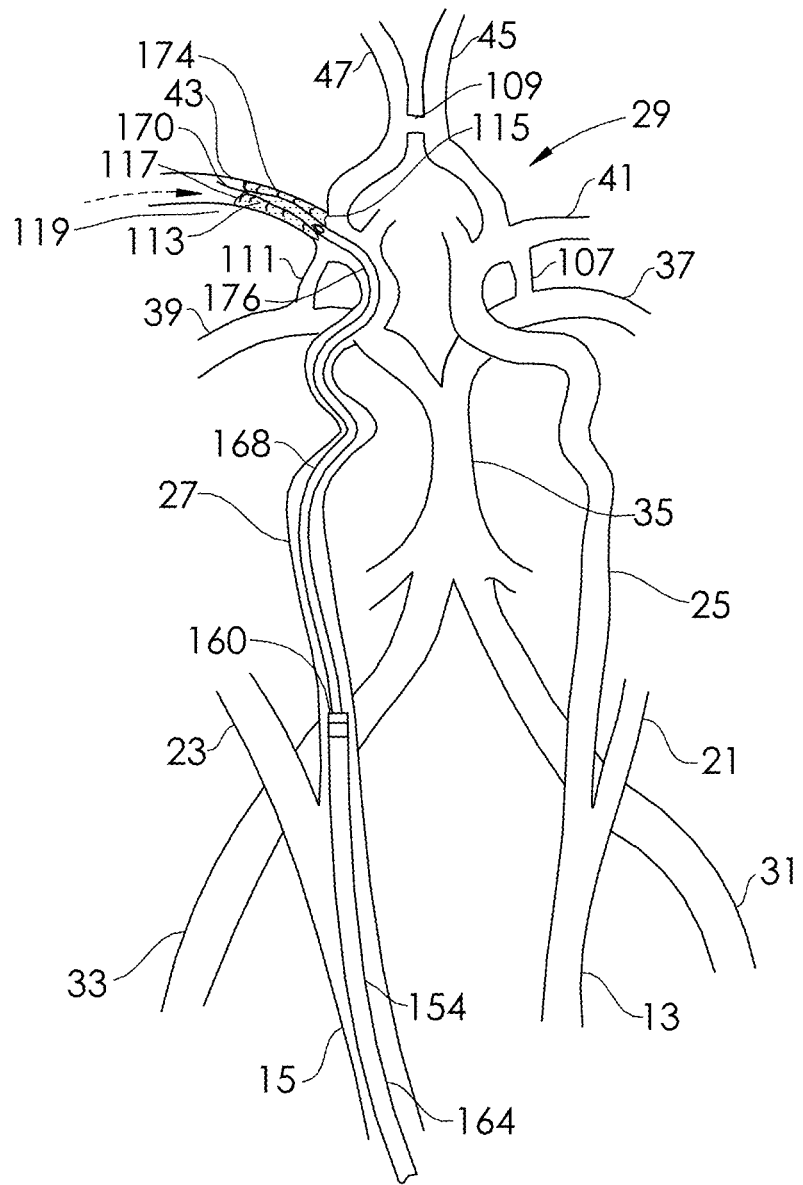
FIG. 14 is a detail view of the thrombus of FIG. 13 treated by a clot removal system in combination with the occlusion perfusion system of FIGS. 11-12, according to an embodiment of the present disclosure.

Oftentimes, thrombi 113 in distal locations in the Circle of Willis 29, such as the middle cerebral arteries 41, 43, are difficult to access with interventional catheters 168. Removing the thrombi 113 with interventional catheters 168 can allow the recovery from a stroke, with the reopened artery able to supply oxygenated blood to brain tissue that had not been receiving a sufficient amount. However, even if the location can be reached with an interventional catheter 168, the act of removing the thrombus with a clot retrieval device or an aspiration catheter may cause some of the thrombus 113 to migrate to a different cerebral artery, and potentially cause another stroke, possibly a stroke in a more critical portion of the brain 1, thus risking death or further disability. FIG. 14 illustrates an interventional catheter 168 comprising a clot retriever 174 at its distal end 176 that has been inserted through the lumen 160 of the guiding catheter 154 and into the right middle cerebral artery 43 that is occluded by the thrombus 113. Retrograde flow (dashed arrow) of oxygenated arterial blood is supplied from the lumen 48 of the occluding perfusion catheter 40 (straight arrow, FIG. 12), and is thus able to perfuse brain tissue 119, in spite of the occlusion of the right middle cerebral artery 43 by the thrombus 113. Thus, by first performing steps 202-210 of the method 200 of FIG. 8, a user can begin perfusion of the brain tissue 119 of a stroke patient as early as possible after patient's entry into the hospital or medical facility. Subsequently, the interventional catheter 168 is placed as part of the system for performing a cerebral intervention 150 to carefully and efficiently remove the thrombus 113. The retrograde perfusion provided by the occluding perfusion system 100 affords the user the time to perform the procedure in an optimum manner, lowering the likelihood of complications. Maintenance of a superior vena caval pressure of between about 15 mm Hg and about 25 mm Hg has been reported to minimize brain edema during retrograde brain perfusion. Retrograde cerebral perfusion that is maintained at an internal jugular vein pressure of between about 15 mm Hg and about 25 mm Hg would be expected to substantially deliver oxygenated blood into the brain tissue. The diameter and the length of the lumen 48 of the occluding perfusion catheter 40 can be configured such that, even with the addition the additional flow resistance provided by the lumen 48, the delivery of oxygenated blood can be maintained at least at about 15 mm Hg, or at least at about 20 mm Hg, or at least at about 25 mm Hg. In other words, if an arterial pressure, or something close to arterial pressure, is being applied by the blood at the inlet 88 of the proximal female luer 86, then a significant pressure drop is still acceptable, as long as the right internal jugular vein 77 at the distal opening 90 is capable of achieving the pressure of between about 15 mm Hg and about 25 mm Hg. This is of course while the occlusion balloon 68 is occluding the right internal jugular vein 77. Thus, passive shunting of arterial blood is achieved at an effective level. For a short procedure, the 15-25 mm Hg target may not be necessary, and a lower target for a short time may be the goal, if it at least supplies some reduction in ischemia. For example, at least about 10 mm Hg over 30 minutes.

The lumen 48 has a length between its proximal end and its distal end and one or more transverse dimensions along its length, thus creating a cylindrical cross-sectional lumen area. By standard Hagen-Poiseuille calculations, at least the length and the one or more transverse dimensions of the lumen 48 together provide an overall flow resistance. The overall flow resistance thus leads to a particular pressure drop or pressure head loss across the length of the lumen 48, depending on the viscosity of the blood (blood is generally non-Newtonian), and the particular pressure applied at the inlet 88. In some embodiments, it is desired that the lumen 48 causes a pressure head loss of less than 95 mm Hg when blood having a temperature of between about 35° C. and about 39° C. is allowed to pass through the lumen 48 from its proximal end to its distal end with a mean pressure at the proximal end of the blood perfusion lumen of 110 mm Hg. The lumen 48 is thus designed with an appropriate length and one or more diameters along its length to achieve this goal, such that the arterial blood perfused retrogradely through the internal jugular vein is at a pressure of between about 15 mm Hg and about 25 mm Hg. In some embodiments, the pressure head loss is between about 10 mm Hg and about 95 mm Hg, or between about 25 mm Hg and about 95 mm Hg, or between about 45 mm Hg and about 95 mm Hg, or between about 20 mm Hg and about 60 mm Hg. The lumen 48 may have a total length of between about 50 cm and about 90 cm, or between about 60 cm and about 80 cm. The lumen 48 may have a diameter of between about 1 mm and about 6 mm. If the lumen 48 does not have a circular cross-section, the lumen 48 may have a hydraulic diameter of between about 1 mm and about 6 mm. Hydraulic diameter is a common calculation defined as four times the cross-sectional area, divided by the cross-sectional luminal perimeter (i.e., the "wetted" perimeter).

Figure 15:
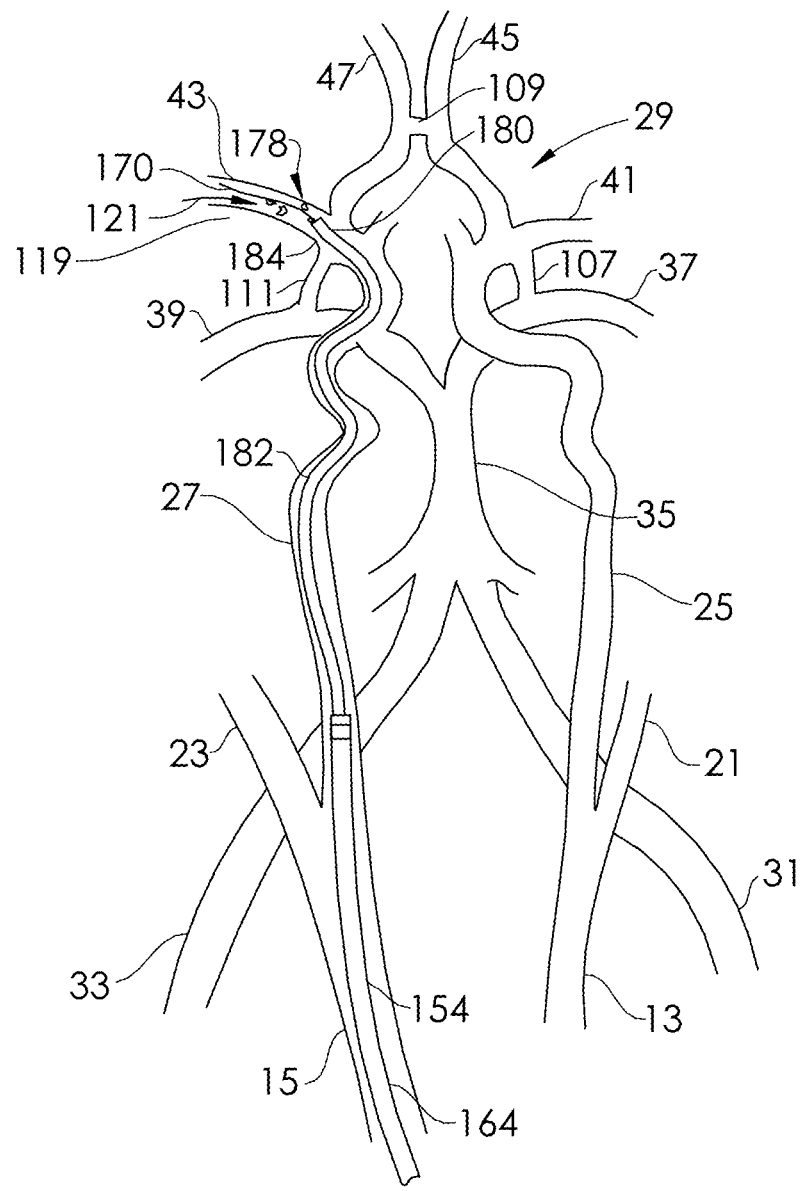
FIG. 15 is a detail view of residual clot being removed during use of the occlusion perfusion system of FIGS. 11-12, according to an embodiment of the present disclosure.

Turning to FIG. 15, in some cases, small pieces of thrombus 178 are present in the right middle cerebral artery 43. This may be the state of the right middle cerebral artery 43 at the beginning of the intervention, or it may be a result of an incomplete removal of the thrombus 113 of FIG. 14. Either way, the pieces of thrombus 178 may be in danger of being dislodged by a catheter or guidewire, or even naturally dislodged, for example, by a change in flow conditions, such as an increase in arterial blood pressure or an increase in arterial flow rate, or heart rate. A dislodged piece of thrombus 178 may occlude the right middle cerebral artery 43 at a location downstream or may occlude another downstream vessel, a side branch, a communicating cerebral artery 107, 109, 111, or one of the anterior cerebral arteries 45, 47 or posterior cerebral arteries 37, 39. In some cases, it may not be necessary to use a capture catheter 182 (FIG. 15), as the one or more pieces of thrombus 178 may be flushed proximally in a vessel of concern (e.g., the right middle cerebral artery 43), and flushed into another vessel of less concern. For example, an artery that feeds a less critical portion of brain tissue. One or more of the pieces of thrombus 178 may be aspirated proximally, toward the distal end 180 of a capture catheter 182 that has been inserted through the guiding catheter 154. The capture catheter 182 may comprise an aspiration catheter having a central lumen to aspirate the pieces of thrombus 178, or may comprise a catheter having a snare at its distal end 180 to snare one or more of the pieces of thrombus 178. In FIG. 15, the distal end 180 of the capture catheter 182 has been inserted at least partially into the right middle cerebral artery 43, past the proximal end 184 of the right middle cerebral artery 43. When the one or more pieces of thrombus 178 are sufficiently captured or aspirated by the capture catheter 182, the capture catheter 182 can be removed from the guiding catheter 154 and from the patient, leaving the right middle cerebral artery 43 and the surrounding vessels open and patent, and allowing normal perfusion of the surrounding brain tissue 119, fed by the arteries of the Circle of Willis 29.

Figure 16:
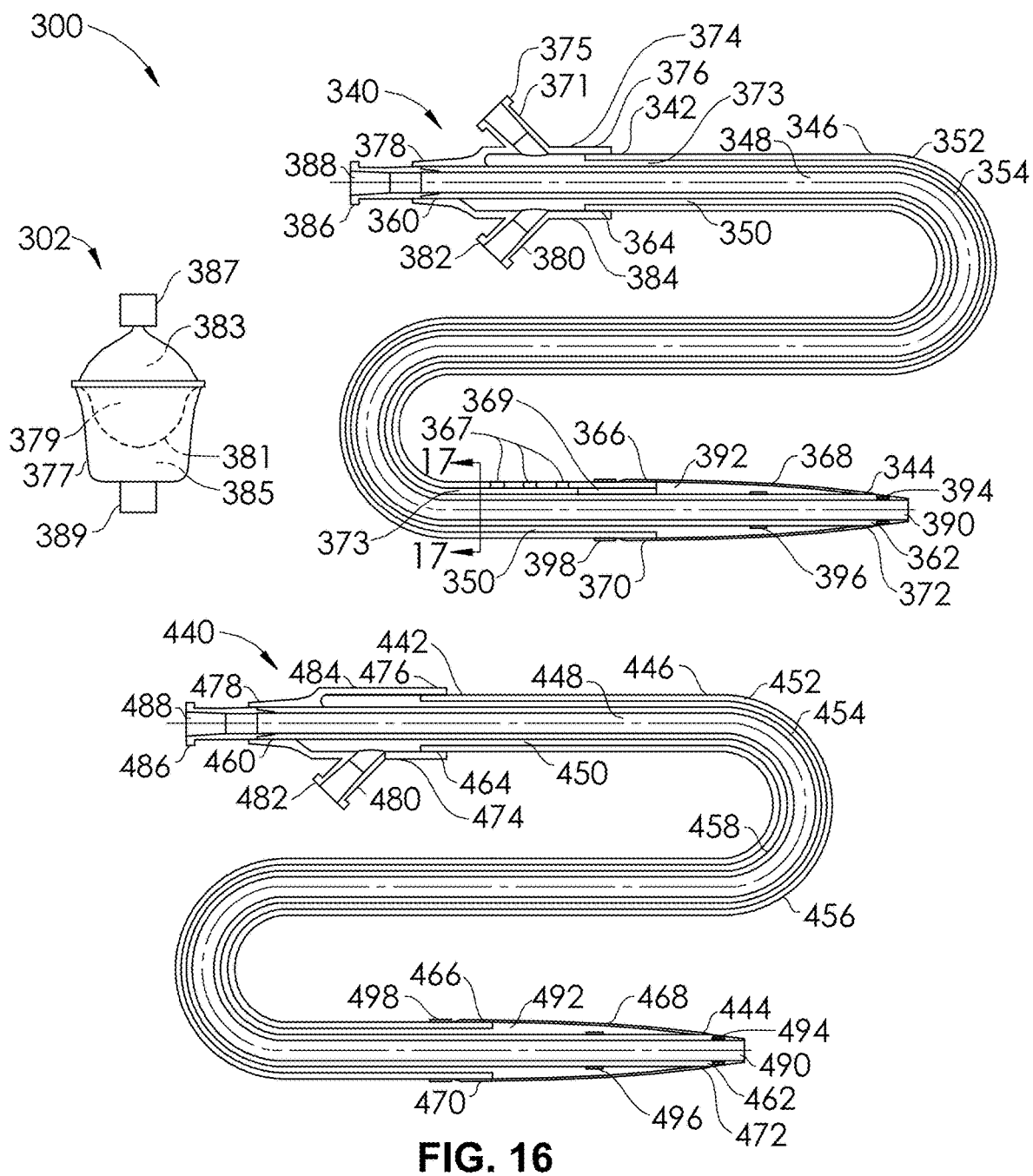
FIG. 16 is a sectional view of a system for performing retrograde perfusion and flow reversal, according to an embodiment of the present disclosure.

FIG. 16 illustrates a system for performing retrograde perfusion and flow reversal 300 comprising a venous occluding perfusion catheter 340, an arterial occluding perfusion catheter 440, and a blood filter 302. The arterial occluding perfusion catheter 440 in configured for placement in an artery, such as an internal carotid artery, and has a similar configuration to the occluding perfusion catheter 40 of FIGS. 3-4, comprising a proximal end 442 and a distal end 444. The arterial occluding perfusion catheter 440 comprises a shaft 446 having a thru lumen 448 and an inflation lumen 450. In some embodiments, the thru lumen 448 and inflation lumen 450 may be arrayed side-by-side in the shaft 446, for example, with each lumen having a D-shapes cross-section, or with one lumen having a circular cross section and the other lumen having a crescent-shaped cross-section. However, in the embodiment illustrated in FIG. 16, the thru lumen 448 has a circular cross-section and the inflation lumen 450 has an annular cross-section, extending around the thru lumen 448. The inflation lumen 450 is contained between an annular outer wall 452 of the shaft 446 and an annular inner wall 454 of the shaft 446. In some embodiments, the outer wall 452 defines an outer tube 456 and the inner wall 454 defines an inner tube 458, inserted within the outer tube 456. The inner tube 458 includes a proximal end 460 and a distal end 462, and the outer tube 456 includes a proximal end 464 and a distal end 466. An occlusion balloon 468 comprises a proximal end 470 sealingly bonded to the distal end 466 of the outer tube 456 and a distal end 472 sealingly bonded to the distal end 462 of the inner tube 458. The proximal end 470 and distal end 472 of the occlusion balloon 468 may be bonded with adhesive, and/or may be wound in place. The occlusion balloon 468 may comprise an elastomeric tube, comprising silicone, urethane, polyether block amide, or another thermoplastic elastomer. FIG. 16 illustrates the occlusion balloon 468 in its deflated state, and it is configured to be expandable in a similar manner to the balloon occlusion balloon 68 in its inflated state in FIG. 4. The occlusion balloon 468 may have an expanded diameter of between about 3 mm and about 10 mm, or between about 5 mm and about 9 mm, or between about 6 mm and about 8 mm.

The outer tube 456 and inner tube 458 may each comprise one or more of the following polymers: polyamide, polyurethane, polyether block amide, polyvinyl chloride, polyethylene, polypropylene, or other polyolefins.

A y-connector 474 is molded or otherwise formed from a rigid polymer such as polycarbonate, and has a distal end 476 that is sealingly bonded to the proximal end 464 of the outer tube 456 and a proximal end 478 that is sealingly bonded to the proximal end 460 of the inner tube 458. A side port 480 comprising a female luer connector 482 extends radially and proximally from a body 484 of the y-connector 474. A proximal female luer 486 is sealingly bonded to the proximal end 478 of the y-connector 474 and/or to the proximal end 460 of the inner tube 458. Thus, the thru lumen 448 extends between the tapered inlet 488 of the proximal female luer 486 to a distal opening 490 at the distal end 444 of the arterial occluding perfusion catheter 440. The thru lumen 448 is configured for the placement of a guidewire (not shown in FIG. 16), but is also configured for the passage of blood. For example, the blood may travel distal to proximal within the thru lumen 448. In some cases, the blood passes through the thru lumen 448 when the guidewire is removed from the thru lumen 448. In some cases, the blood passes through the thru lumen 448 with the guidewire still at least partially, or completely, in place within the thru lumen 448. Different guidewire sizes (outer diameters) may be used, such as 0.012 inch, 0.014 inch, 0.018 inch, 0.021 inch, 0.025 inch, 0.028 inch, 0.032 inch, 0.035 inch, or 0.038 inch. The female luer 482 of the side port 480 is configured for attaching a male luer connector of a syringe or an inflation device, such that inflation fluid such as saline, contrast media, or a mixture or the two, may be injected through the inflation lumen 450 to increase the volume of an interior 492 of the occlusion balloon 468, thus inflating it. The occlusion balloon 468 can be deflated by pulling a negative pressure or evacuating the syringe or inflation device. One or more marker bands 494, 496, 498 may be carried on the arterial occluding perfusion catheter 440 to allow visualization of the area of the occlusion balloon 468 and/or the distal end 444. The marker bands 494, 496, 498 may comprise radiopaque materials, such as platinum, tantalum, gold, or an alloy, such as 90% platinum and 10% iridium. A first marker band 494 is carried on the distal end 444, and may be attached by adhesive or epoxy, or may be swaged, sputtered, heat bonded, or plated in place. A second marker band 496 is carried on the inner tube 458 near the center of the occlusion balloon 468, and may be attached by adhesive or epoxy, or may be swaged, sputtered, heat bonded, or plated in place. A third marker band 498 is carried on the outer tube 456 as shown, or alternatively, the inner tube 458, at or adjacent the proximal end 470 of the occlusion balloon 468, and may be attached by adhesive or epoxy, or may be swaged, sputtered, heat bonded or plated in place. In some embodiments, only the second marker band 496 is necessary, as it demonstrates the location of the center of the occlusion balloon 468. In some embodiments, only the first marker band 494 and the third marker band 498 are necessary, as they demonstrate the general location of the ends of occlusion balloon 468. In some embodiments, only one of the marker bands 494, 498 may be used.

Figure 17A:
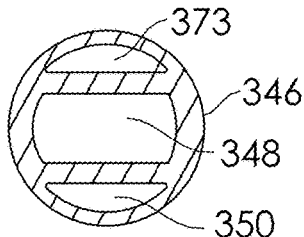
FIG. 17A is a cross-sectional of an occluding perfusion catheter taken along lines 17-17 of FIG. 16.
Figure 17B:
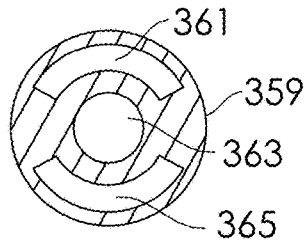
FIG. 17 B is a cross-section of an alternative occluding perfusion catheter.

The venous occluding perfusion catheter 340 in configured for placement in a vein, such as an internal jugular, and has a proximal end 342 and a distal end 344. The venous occluding perfusion catheter 340 comprises a shaft 346 having a thru lumen 348, an inflation lumen 350, and a relief lumen 373. In some embodiments, the thru lumen 348 may be centrally located, and each of the inflation lumen 350 and relief lumen 373 may be laterally arrayed, as shown in FIG. 17A and in an alternative shaft 359 in FIG. 17B, having a circular thru lumen 363, and annular inflation lumen 365 and annular relief lumen 361. Each of the annular inflation lumen 365 and annular relief lumen 361 may extend circumferentially less than 180°, as shown in FIG. 17B. In other embodiments, the inflation lumen 365 and relief lumen 361 each have an annular shape, with one extending less than 180° and the other extending more than 180°. In other embodiments, the thru lumen 348, 363, inflation lumen 350, 365, and relief lumen 373, 361 may be arrayed more evenly in the cross section of the shaft 346, 359. In the embodiment of FIGS. 16-17A, the inflation lumen 350 is contained between an outer wall 352 of the shaft 346 and an inner wall 354 of the shaft 346. The shaft 346 includes a proximal end 360 and a distal end 362. The shaft 346 may be partially skived at each end so that only the inflation lumen 350 and inner walls 354 extend completely, such that the entirety of the shaft 346 has a proximal end 364 and a distal end 366. An occlusion balloon 368 comprises a proximal end 370 sealingly bonded to the distal end 366 of the outer portion of the shaft 346 and a distal end 372 sealingly bonded to the distal end 366 of the shaft 346. The proximal end 370 and distal end 372 of the occlusion balloon 368 may be bonded with adhesive, and/or may be wound in place. The occlusion balloon 368 may comprise an elastomeric tube, comprising silicone, urethane, polyether block amide, or another thermoplastic elastomer. FIG. 16 illustrates the occlusion balloon 368 in its deflated state, and it is configured to be expandable in a similar manner to the balloon occlusion balloon 68 in its inflated state in FIG. 4. The occlusion balloon 368 may have an expanded diameter of between about 6 mm and about 14 mm, or between about 8 mm and about 12 mm.

Though a balloon 368 is described, other non-balloon occlusion elements may be used, including, but not limited to mechanically expandable elements, expandable shape memory polymer elements, polymer elements supported by expandable shape memory alloy structures, or coated self-expanding mesh elements. The shaft 346 comprise one or more of the following polymers: polyamide, polyurethane, polyether block amide, polyvinyl chloride, polyethylene, polypropylene, or other polyolefins.

Figure 18:
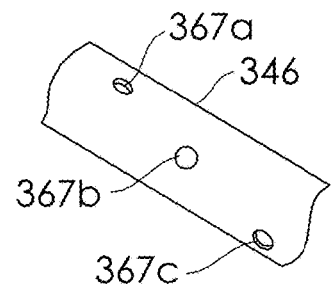
FIG. 18 is a perspective detail view of a shaft of an alternative occluding perfusion catheter, according to an embodiment of the present disclosure.

A y-connector 374 is molded or otherwise formed from a rigid polymer such as polycarbonate, and has a distal end 376 that is sealingly bonded to the shaft 346 and a proximal end 378 that is sealingly bonded to the proximal end 360 of the shaft 346. A first side port 380 comprising a female luer connector 382 extends radially and proximally from a body 384 of the y-connector 374. A second side port 371 comprising a female luer connector 375 extends radially and proximally from the body 384 of the y-connector 374. The first and second side ports 380, 371 are on opposite sides of the y-connector 374, but may alternatively be on the same side and may be longitudinally staggered. A proximal female luer 386 is sealingly bonded to the proximal end 378 of the y-connector 374 and/or to the proximal end 360 of the shaft 346. Thus, the thru lumen 348 extends between the tapered inlet 388 of the proximal female luer 386 to a distal opening 390 at the distal end 344 of the venous occluding perfusion catheter 340. The thru lumen 348 is configured for the placement of a guidewire (not shown in FIG. 16), but is also configured for the passage of blood. For example, the blood may travel proximal to distal within the thru lumen 348. In some cases, the blood passes through the thru lumen 348 when the guidewire is removed from the thru lumen 348. In some cases, the blood passes through the thru lumen 348 with the guidewire still at least partially, or completely, in place within the thru lumen 348. Different guidewire sizes (outer diameters) may be used, such as 0.012 inch, 0.014 inch, 0.018 inch, 0.021 inch, 0.025 inch, 0.028 inch, 0.032 inch, 0.035 inch, or 0.038 inch. The thru lumen 348, 363 may have similar lengths and diameters/hydraulic diameters as the lumen 48 of the occluding perfusion catheter 40 of FIG. 3. The female luer 382 of the first side port 380 is configured for attaching a male luer connector of a syringe or an inflation device, such that inflation fluid such as saline, contrast media, or a mixture or the two, may be injected through the inflation lumen 350 to increase the volume of an interior 392 of the occlusion balloon 368, thus inflating it. The occlusion balloon 368 can be deflated by pulling a negative pressure or evacuating the syringe or inflation device. The female luer 375 of the second side port 371 is configured for attaching a male luer connector, as will be described in relation to FIG. 19, for allowing arterial blood to travel through the relief lumen 373, from proximal to distal, and out one or more ports 367 (holes, openings, apertures) in the outer wall 352 of the shaft 346, the ports 367 thus communicating with the relief lumen 373. A filling material 369 blocks the relief lumen 373 distal to the ports 367 so that all of the blood (or other fluid) passing through the relief lumen 373 exits the ports 367 and into a blood vessel (e.g., internal jugular vein). The filling material 369 may comprise an adhesive, epoxy, or hot melt, or alternatively may be replaced by heat forming the walls of the shaft 346 to close the relief lumen 373 distally. In some embodiments, the ports 367 may comprise a single port. Although the ports 367 in FIG. 16 comprise three ports arrayed longitudinally, an alternative embodiment, shown in FIG. 18, illustrates three ports 367a-c arranged in a helical array, such that each port 367 is at a different longitudinal location and at a different circumferential location. Each of the ports 367 may have a diameter (if circular) or hydraulic diameter (if not circular) of between about 0.003 inch to about 0.045 inch, or between about 0.005 inch to about 0.025 inch. Each of the ports 367 may have a cross-sectional area of between about 0.0045 mm$^2$ to about 1.3 mm$^2$, or between about 0.0126 mm$^2$ to about 0.4 mm$^2$.

One or more marker bands 394, 396, 398 may be carried on the venous occluding perfusion catheter 340 to allow visualization of the area of the occlusion balloon 368 and/or the distal end 344. The marker bands 394, 396, 398 may comprise radiopaque materials, such as platinum, tantalum, gold, or an alloy, such as 90% platinum and 10% iridium. A first marker band 394 is carried on the distal end 344, and may be attached by adhesive or epoxy, or may be swaged, sputtered, heat bonded, or plated in place. A second marker band 396 is carried on the shaft 346 near the center of the occlusion balloon 368, and may be attached by adhesive or epoxy, or may be swaged, sputtered, heat bonded, or plated in place. A third marker band 398 is carried on the shaft 346 at or adjacent the proximal end 370 of the occlusion balloon 368, and may be attached by adhesive or epoxy, or may be swaged, sputtered, heat bonded or plated in place. In some embodiments, only the second marker band 396 is necessary, as it demonstrates the location of the center of the occlusion balloon 368. In some embodiments, only the first marker band 394 and the third marker band 398 are necessary, as they demonstrate the general location of the ends of occlusion balloon 368. In some embodiments, only one of the marker bands 394, 398 may be used.

The blood filter 302 comprises a casing 377 having an interior 379. Filter media 381 separates the interior 379 into an inflow side 383 and an outflow side 385. An inflow port 387 allows blood to enter, and an outflow port 389 allows blood that has been filtered by the filter media 381 to exit. The ports 387, 389 may each comprise a male or female luer connector, or a barbed connector, or another type of flared interface.

Figure 19:
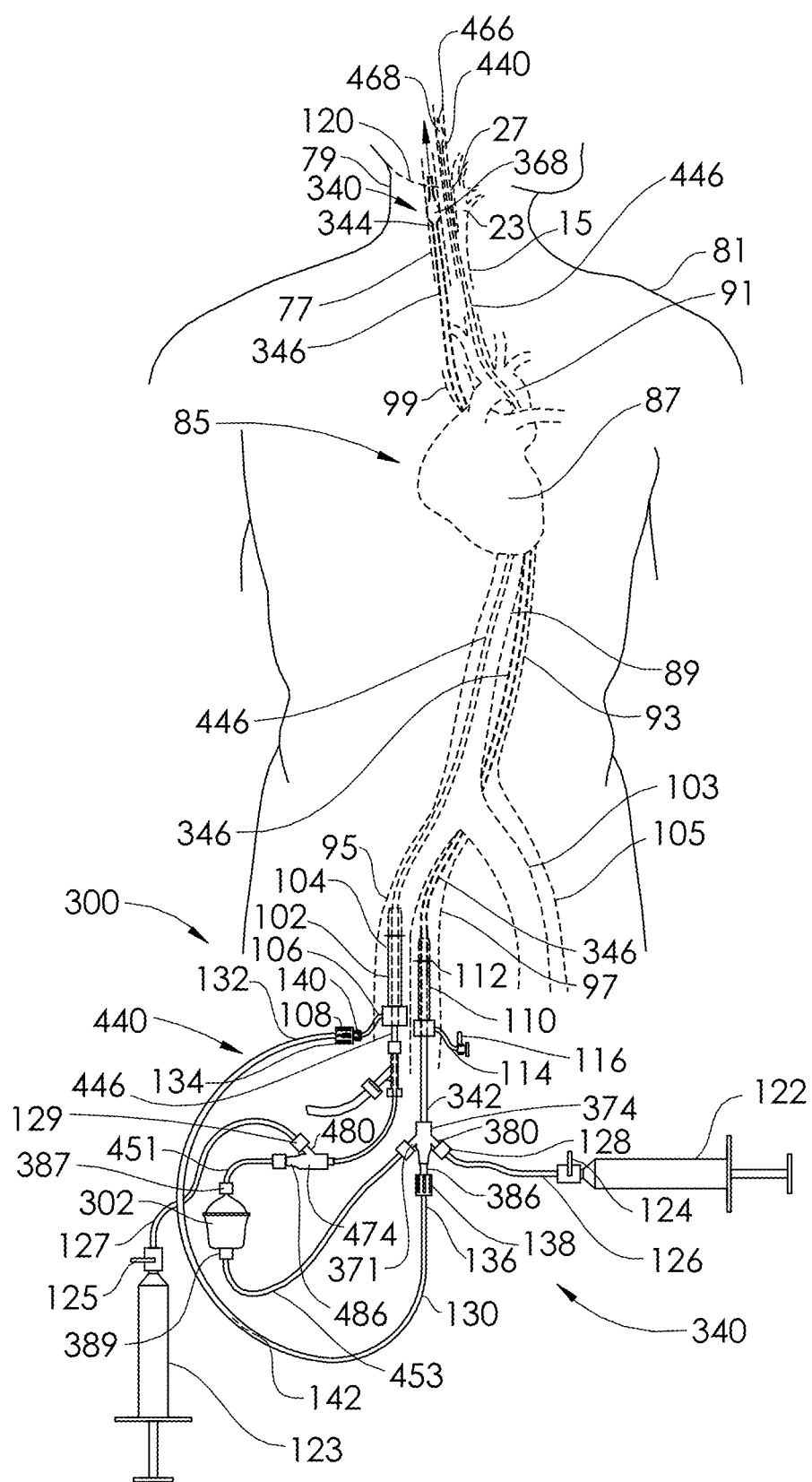
FIG. 19 is a view of a system for performing a retrograde perfusion and flow reversal, according to an embodiment of the present disclosure.
Figure 20:
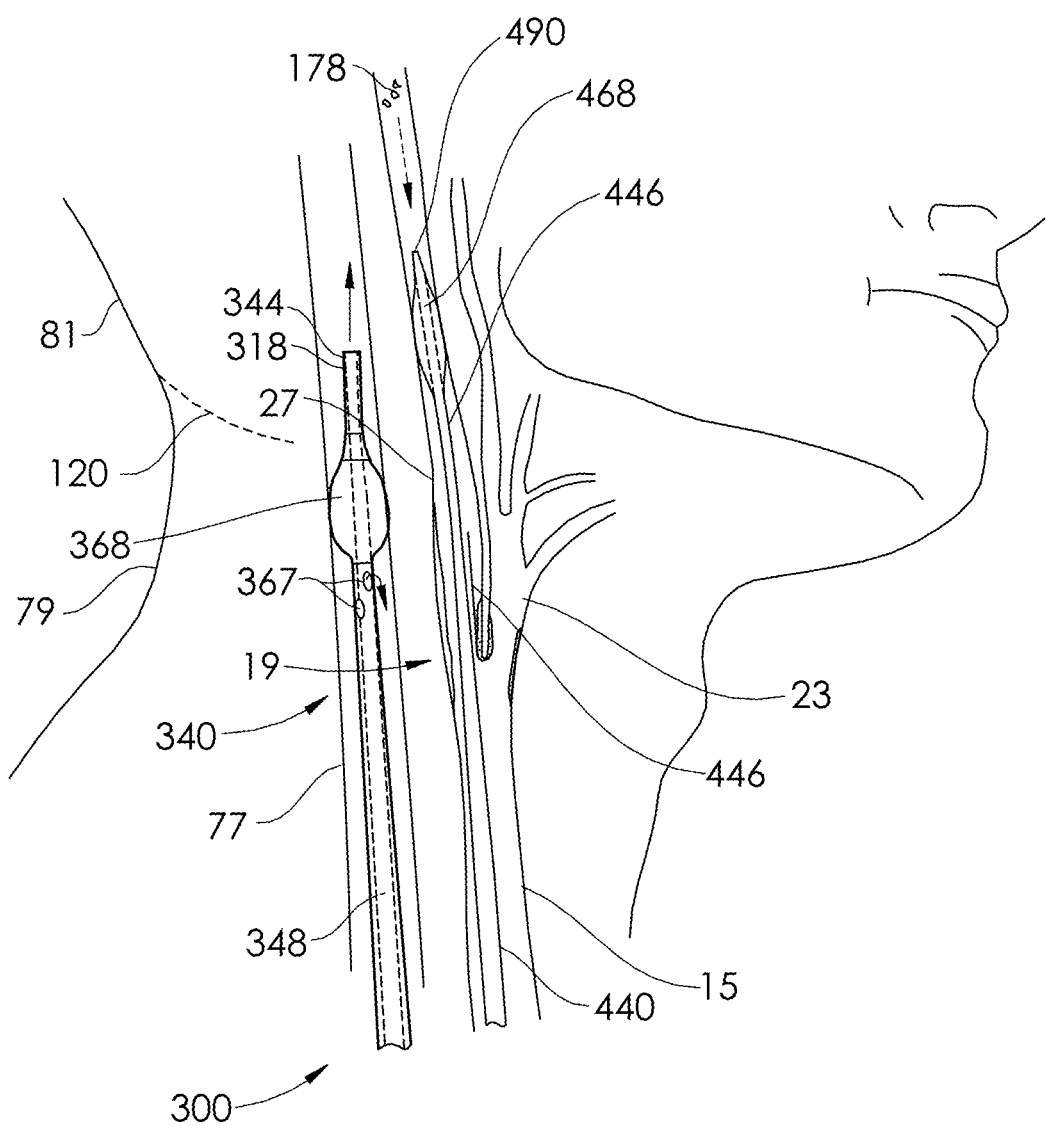
FIG. 20 is a detail view of the occlusion perfusion system of FIG. 19 in operation during a procedure involving the Circle of Willis.

FIG. 19 illustrates the system for performing a retrograde perfusion and flow reversal 300 assembled in a patient 81 to create flow reversal, as shown by dashed arrow in FIG. 20. The flow reversal may be utilized to protect brain tissue on the arterial side, and may also be utilized to force or push one or more of the pieces of thrombus 178 proximally in the Circle of Willis. In some cases, it may not be necessary to use a capture catheter 182 (FIG. 15), as the one or more pieces of thrombus 178 may be flushed proximally in a vessel of concern (e.g., the right middle cerebral artery 43), and flushed into another vessel of less concern. For example, an artery that feeds a less critical portion of brain tissue.

Figure 23:
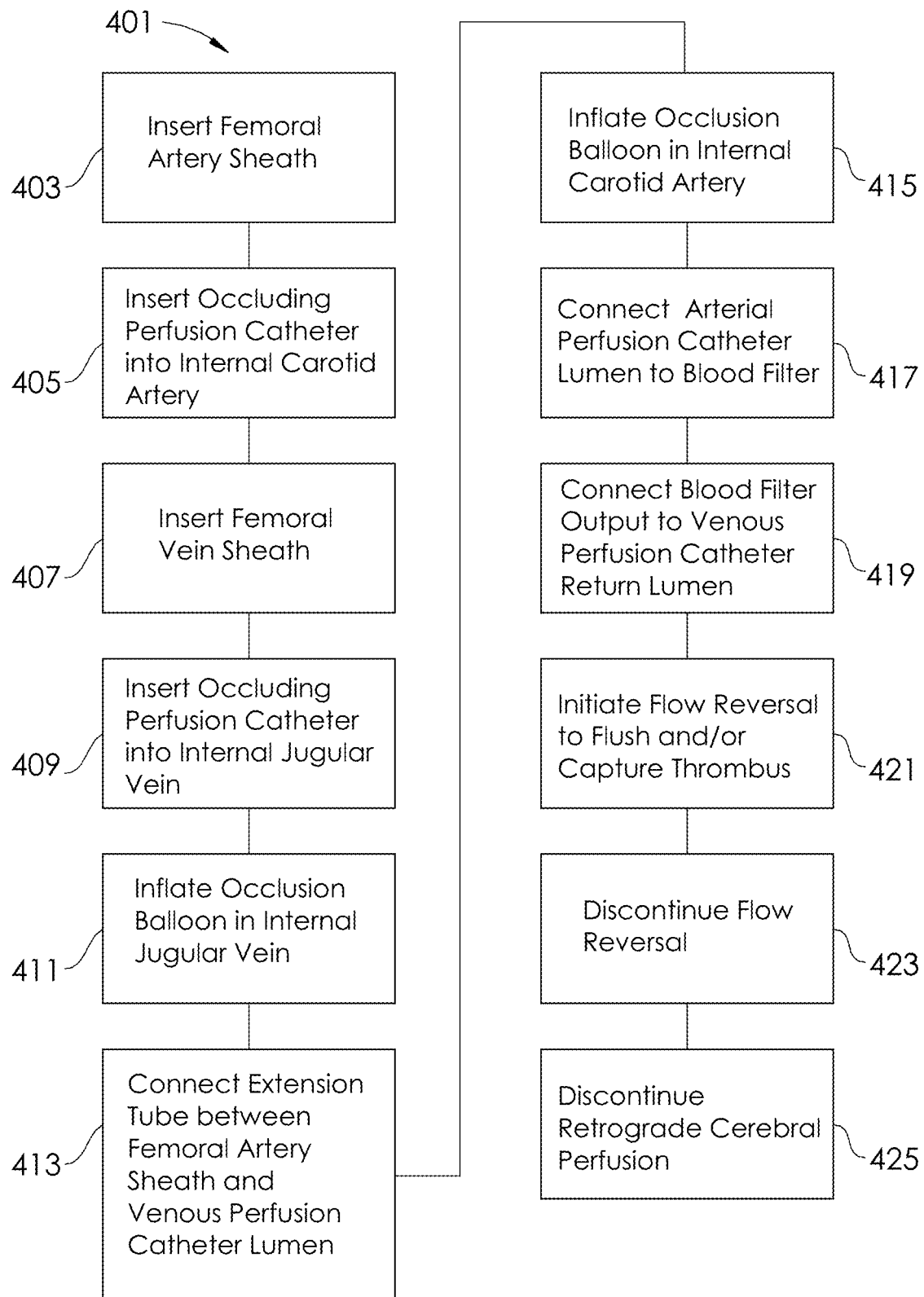
FIG. 23 is a block diagram of a method for performing retrograde perfusion and flow reversal using the system for performing retrograde perfusion and flow reversal of FIG. 19 or the system for performing retrograde perfusion and flow reversal of FIG. 21, according to an embodiment of the present disclosure.

The system for performing a retrograde perfusion and flow reversal 300 is used in accordance with a method 401 for performing retrograde perfusion and flow reversal, as diagrammed in FIG. 23. In step 403, a user inserts an introducer sheath 102 into the right femoral artery 95 through a first insertion site 104 (e.g. puncture), using a percutaneous Seldinger technique. The introducer sheath 102 may comprise an 8 F (French size) short sheath, but may comprise other sizes (e.g., 6 F to 10 F, or 7 F to 9 F), or other lengths. The introducer sheath 102 includes a side port 106 having a stopcock 108. The stopcock 108 is shown in the open position in FIG. 19. In step 405, the user inserts the arterial occluding perfusion catheter 440 through the introducer sheath 102, and advances the distal end 444 into the right internal carotid artery 27. In step 407, the user inserts an introducer sheath 110 into the right femoral vein 97 through a second insertion site 112 (e.g. puncture), using a percutaneous Seldinger technique. The introducer sheath 110 may comprise a 10 F (French size) short sheath, but may comprise other sizes (e.g., 7 F to 12 F, or 9 F to 11 F), or other lengths. The introducer sheath 110 includes a side port 114 having a stopcock 116. The stopcock 116 is shown in the closed position in FIG. 19. In step 409, the user inserts the venous occluding perfusion catheter 340 through the venous-placed introducer sheath 110, and advances the distal end 344 of the venous occluding perfusion catheter 340 through the inferior vena cava 93, the right atrium (not shown) of the heart 87, the superior vena cava 99, the right brachiocephalic vein (not shown) and into an internal jugular vein, in the case of FIGS. 19-20, the right internal jugular vein 77. Alternatively, or additionally, the left femoral artery 103 may be used for placement of the arterial sheath 102, or to place a second arterial sheath. Alternatively, or additionally, the left femoral vein 105 may be used for placement of the venous introducer sheath 110. In some catheter, the venous introducer sheath 110 may be avoided, skipping step 407, and the venous occluding perfusion catheter 340 may be inserted directly through the second insertion site 112. Either way, the venous occluding perfusion catheter 340 may comprise a size of between 7 F and about 12 F, or between 8 F and 10 F. The distal end 344 of the venous occluding perfusion catheter 340 includes an atraumatic distal tip 318 (FIG. 20). In step 409, the venous occluding perfusion catheter 340 is advanced by the user such that the distal tip 318 is located approximately at the skull base 120.

In step 411, the user inflates the occlusion balloon 368 of the venous occluding perfusion catheter 340 with a syringe 122 or other inflation device, such that the occlusion balloon 368 occludes the right internal jugular vein 77. A stopcock 124 attached to the syringe 122 may then be closed, as shown in FIG. 19, to hold the desired balloon inflation volume or balloon inflation pressure. An extension tube 126 having a male luer 128 is shown in FIG. 19 with the male luer 128 coupled to the side port 380 of the y-connector 374 of the venous occluding perfusion catheter 340. The extension tube 126 is shown in FIG. 19 extending between the stopcock 124 and side port 380 but alternatively, the stopcock 124 may be located at the male luer, 128, or may be a separate component that is attachable to the male luer 128 and to the side port 380. In step 413, the user attaches an extension tube 130 between the arterial introducer sheath 102 and the venous occluding perfusion catheter 340. The extension tube 130 has a first end 132 having a first male luer 134 and a second end 136 having a second male luer 138. The first male luer 136 is coupled to a female luer 140 at the side port 106 of the introducer sheath 102 and the stopcock 108 is opened, allowing arterial blood to flow from the right iliac artery (or inferior vena cava, if the sheath 102 is not a short sheath) so that the blood fills the lumen 142 of the extension tube 130 of to the end of the second male luer 138. The second male luer 138 is then attached to the proximal female luer 386 of the y-connector 374 of venous occluding perfusion catheter 340. Arterial blood from the right iliac artery is now passively shunted through the thru lumen 348 venous occluding perfusion catheter 340 and retrogradely through the right internal jugular vein 77, thus feeding tissue of the brain 1 with oxygenated blood. Thus, the reverse flow (straight arrow, FIG. 20) is successfully achieved in a passive manner, as previously described.

In step 415, the user inflates the occlusion balloon 468 of the arterial occluding perfusion catheter 440 with a syringe 123 or other inflation device attached to the sideport 480 if the y-connector 474, such that the occlusion balloon 468 occludes the right internal carotid artery 27 (see FIG. 20). A stopcock 125 attached to the syringe 123 may then be closed, as shown in FIG. 19, to hold the desired balloon inflation volume or balloon inflation pressure. An extension tube 127 having a male luer 129 is shown in FIG. 19 with the male luer 129 coupled to the side port 480 of the y-connector 474 of the arterial occluding perfusion catheter 440. The extension tube 127 is shown in FIG. 19 extending between the stopcock 125 and side port 480 but alternatively, the stopcock 125 may be located at the male luer, 129, or may be a separate component that is attachable to the male luer 129 and to the side port 480. Thus, flow reversal has been achieved that includes both the reversed flow direction in the right internal jugular vein 77 (solid straight arrow, FIG. 20) and a reverse flow direction in the right internal carotid artery 27 (dashed arrow, FIG. 20). Because the Circle of Willis 29 is capable of reversing and generally changing the direction of flow, the occlusion of the right internal carotid artery 27 does not necessarily stop the inherent arterial-supplied flow of oxygenated blood to the brain, because the left internal carotid artery 25 and the basilar artery 35/vertebral arteries 31, 33 are also feeding conduits. In step 417, the user attaches an extension tube 451 between the proximal female luer 486 of the y-connector 474 and inflow port 387 of the blood filter 302. In some embodiments, the extension tube 451 may be prepackaged with the blood filter 302. Arterial blood from the right internal carotid artery 27, distal to the occlusion balloon 486 can now pass from the distal opening 490 at the distal end 444 of the arterial occluding perfusion catheter 440, through the thru lumen 448 (distal to proximal), out the female luer 486, and through the extension tube 451 and blood filter 302. For ease of attachment, the blood filter 302 may be prepackaged with the extension tube 451 and another extension tube 453 that is configured to be coupled between the outflow port 389 of the blood filter 302 and the sideport 371 of the y-connector 374 of the venous occluding perfusion catheter 340. In step 419, after allowing the arterial blood to prime the blood filter 302 and the extension tubes, 451, 453, the user attaches the extension tube 453 to the sideport 371 of the y-connector 374 of the venous occluding perfusion catheter 340.

In step 421, user opens any closed stopcocks or removes any clamps to initiate flow reversal. As long as the blood pressure of the right internal carotid artery 27 distal to the inflated occlusion balloon 486 is greater than the blood pressure of the right internal jugular vein 77 proximal to the inflated occlusion balloon 386, arterial blood from the right internal carotid artery 27 will now be filtered by the blood filter 302 and will then flow from proximal to distal through the relief lumen 373 of the arterial occluding perfusion catheter 440 and out the one or more ports 367 into the right internal jugular vein 77, proximal to the inflated occlusion balloon 386. Thus, via a second arterial-to-venous shunt, excess blood in the arterial circulation of the head and neck is capable of draining to the central venous system, protecting the arteries of the head and neck from excessive pressure or stress. In addition, one or more pieces of thrombus 178 may be forced by the retrograde flow (dashed arrow, FIG. 20) into the distal opening 490 of the arterial occluding perfusion catheter 440, passing through the thru lumen 448 and into the blood filter 302, where the one or more pieces of thrombus 178 are caught. Thus, only filtered blood is sent through the thru lumen 348 and out the ports 367 into the right internal jugular vein 77. The one or more pieces of thrombus 178 are thus removed from the right internal carotid artery 27, and thus removed from the vasculature of the patient 81. When the procedure is complete, the user discontinues flow reversal in step 423, by deflating the occlusion balloon 386, or by closing one or more stopcocks or valves, or attaching a clamp, and/or by disconnecting one or more of the blood filter 302 or the extension tubes 451, 453. Then, in step 425, the user discontinues retrograde cerebral perfusion, by deflating the occlusion balloon 486, or by closing a stopcock, or by detaching the extension tube 130. At the end of any of the methods or procedures described herein, the user may choose to perform an intracranial angiogram to verify the success of the intervention.

Figure 21:
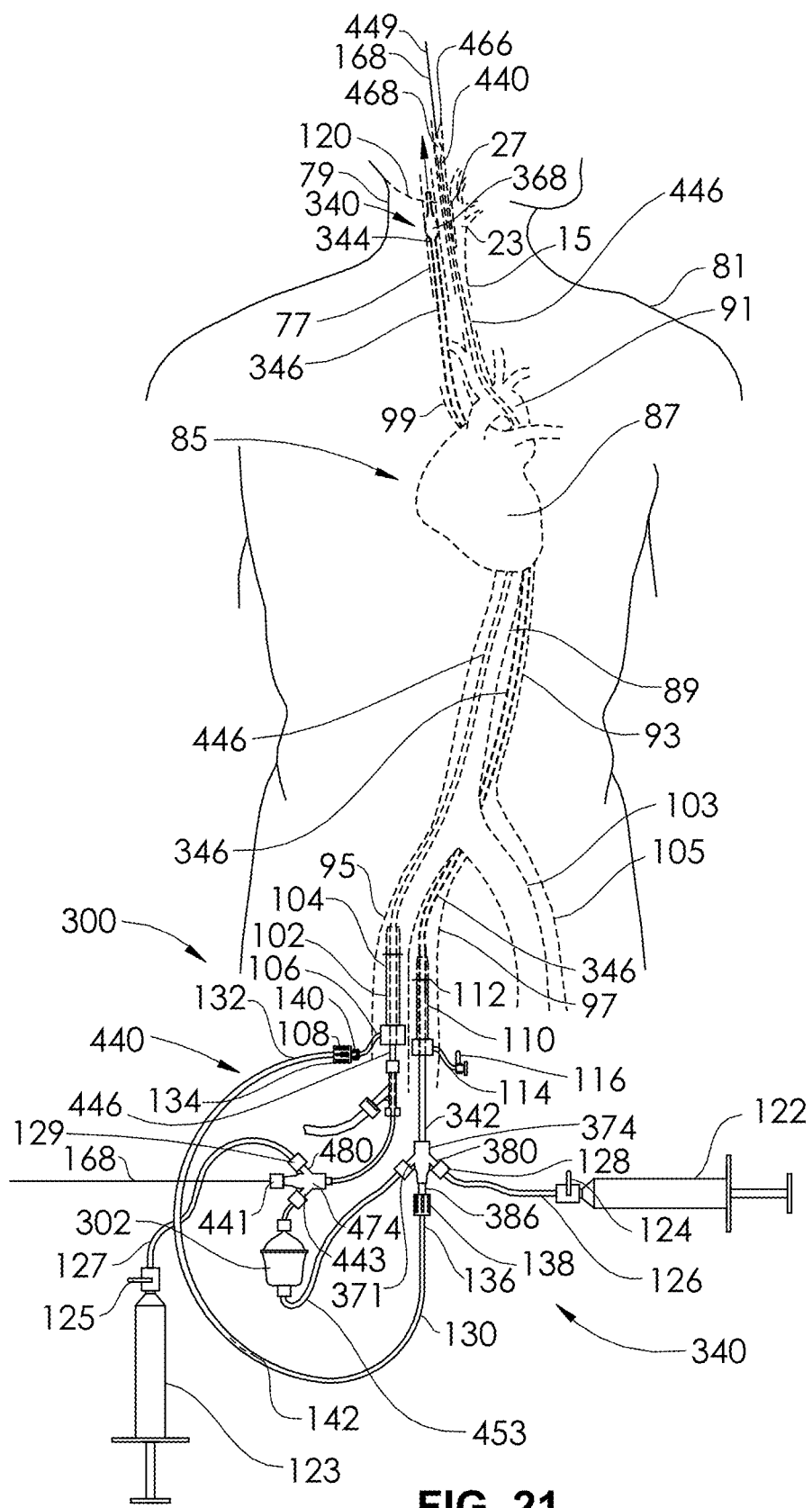
FIG. 21 is a view of a system for performing a retrograde perfusion and flow reversal, according to an embodiment of the present disclosure.
Figure 22:
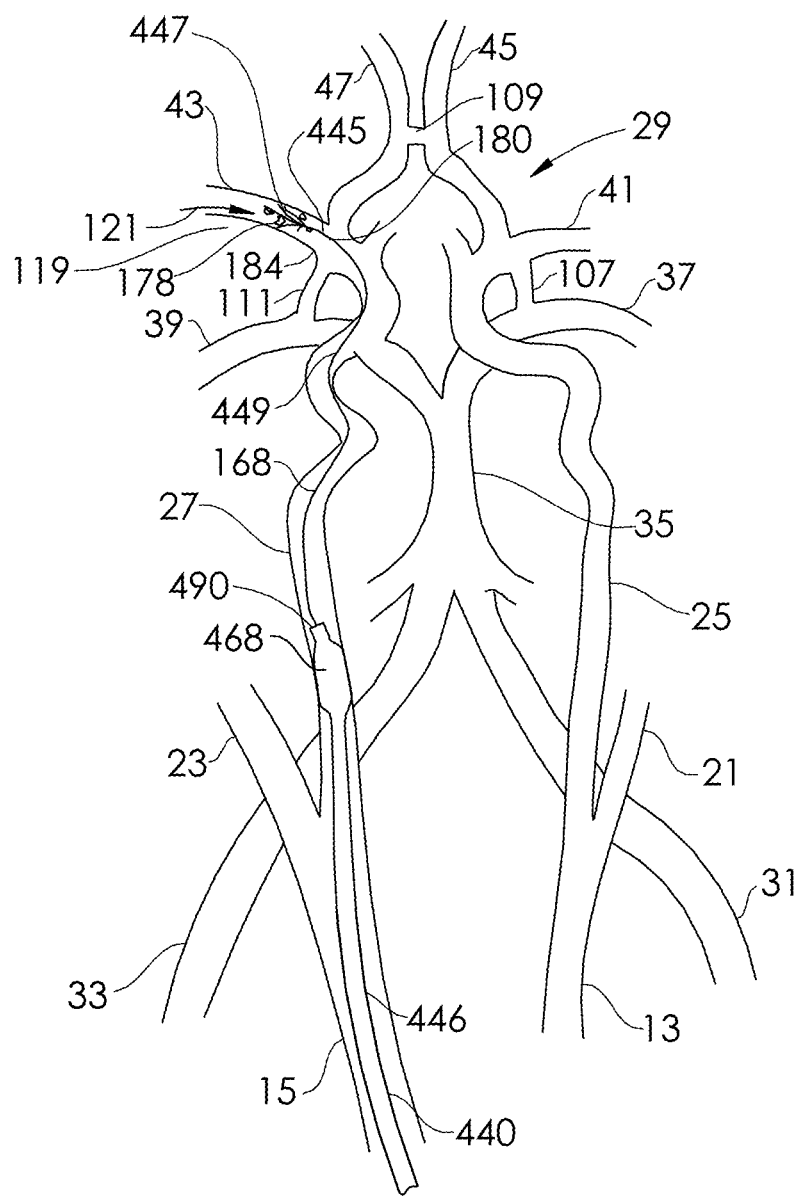
FIG. 22 is a detail view of residual clot being pushed proximally by the system for performing retrograde perfusion and flow reversal of FIG. 21, according to an embodiment of the present disclosure.

FIG. 21 illustrates the system for performing a retrograde perfusion and flow reversal 300 used in accordance with the method 401 for performing retrograde perfusion and flow reversal. However, in step 421, the user places an interventional catheter 168 through the thru lumen 448 of the arterial occluding perfusion catheter 440 to perform an intervention in an artery of the Circle of Willis 29, such as the right middle cerebral artery 43 (FIG. 22). The interventional catheter 168 comprises an elongate wire 449 having a snare 447 at its distal end 445. The wire 449 may have a small diameter between about 0.010 inch and about 0.025 inch, so that it does not significantly increase flow resistance through the thru lumen 448, such that blood may flow efficiently with the wire 449 in place. The y-connector 474 of the arterial occluding perfusion catheter 440 has been modified so that the thru lumen 448 connects to a side port 443 instead of the proximal female luer 486. In place of the proximal female luer 486 is a hemostasis valve (e.g., Touhy-Borst) 441 that also communicates with the thru lumen 448. Thus, the interventional catheter 168 is placed through the hemostasis valve 441 and through the thru lumen 448. The blood filter 302 is coupled to the side port 443 to receive the arterial blood that flows distal to proximal through the thru lumen 448, and over the wire 449 (or shaft) of the interventional catheter 168. By fluoroscopic guidance or other visualization technique (CT, Mill, ultrasound, etc.), the user manipulates the snare 447 of the interventional catheter 168 to retrieve the one or more pieces of thrombus 178.

Thus, the combination of the snare 447 and the reverse flow 121 control the capture of the one or more pieces of thrombus 178, without risking that the one or more pieces of thrombus 178 enter the right internal carotid artery 27, the right posterior communicating artery 111, or the right anterior cerebral artery 47. It is expected that achieving a pressure of between about 15 mm Hg and about 25 mm Hg in the right internal jugular vein 77 at the distal opening 390 of the venous occluding perfusion catheter 340 will be sufficient to move the one or more pieces of thrombus 178 as desired. However, in some cases, a higher pressure may be utilized. In some embodiments, either the diameter of the lumen 348 can be increased and/or the length of the lumen 348 can be shortened to configured the venous occluding perfusion catheter 340 such that the addition the additional flow resistance provided by the lumen 348 creates less of a pressure drop, allowing an even higher driving pressure in the right internal jugular vein 77. Returning to FIG. 9, it is possible to monitor retrograde perfusion pressure in any embodiment of the present disclosure by connecting a stopcock 137 between the second male luer 138 of the extension tube 130 and the proximal female luer 86, 386 of the y-connector 74, 374. The stopcock 137, as shown in FIG. 9 is a four-way stopcock in the fully open position. A pressure gauge 141 is hydraulically coupled to the stopcock 137 by an extension tube 139. Thus, the pressure gauge 141 measures the applied (arterial) pressure at the proximal female luer 86, 386, prior to the pressure drop through the thru lumen 48, 348. By knowing the general amount of pressure drop, the measurement of the pressure gauge 141 can be calibrated to allow general confirmation of the amount of perfusion achieved. The pressure gauge 141 may be an analog gauge (as shown) or may be a digital gauge. In other embodiments, the pressure gauge 141 may replaced by a flow rate gauge.

Distal carotid occlusion, distal protection devices, or distal temporary filters may potentially be avoided during interventions, because some reversed flow may be achievable in the right internal carotid artery 27 via the retrograde flow alone (dashed arrow, FIG. 20). Thus, any portion of atherosclerotic plaque that may break off during stenting may be stopped from flowing downstream (toward the brain tissue), thus protecting it. In some cases, emboli or thromboemboli may be sent in a reverse direction, away from the brain tissue. Certain segments of the middle cerebral artery, such as the M3 or M4 segments, are common locations where thrombus can lodge, and where current snare or retrieval devices oftentimes have difficulty reaching. Controlling and manipulating the blood flow in the Circle of Willis 29 using the embodiments described herein is an additional tool that allows blood pressure and blood flow to perform what a medical device cannot do directly. The setup and operation of the system for performing a retrograde perfusion and flow reversal 300 for a patient presenting with thromboembolic stroke is feasible in a total procedural length of 30 minutes or less, or even 20 minutes or less. Once the flow reversal is initiated, the user may choose to allow three to five minutes to go by, and then perform a short angiogram to determine whether the one or more pieces of thrombus 178 have cleared by nature of the flow reversal alone. If not, another three to five minutes of flow reversal may be performed, and another angiogram obtained. The user may the determine whether it is necessary to take a more invasive strategy, such as the use of the interventional catheter 168 of FIG. 21-22. For example, the thrombus 178 may have been transported proximally, so that it is no longer in a difficult to reach area, and thus has become accessible by an interventional catheter 168.

Some interventionists may be less likely than others to attempt flow reversal as described herein, or may be less likely to use it in certain clinical situations. The method 200 described in FIG. 8, performed without the flow reversal described in the method 401 of FIG. 23, may in some cases be effective on its own in clearing emboli from cerebral vessels. An embolus in the M1 segment of the middle cerebral artery (MCA), or an embolus at the T-junction (internal carotid artery/middle cerebral artery/anterior cerebral artery) may be proximal enough to be manipulated by flow alone, using retrograde perfusion, and without using flow reversal. The user may puff contrast into the internal carotid artery during the retrograde perfusion procedure, for example, through the lumen 160 of the guiding catheter 154 (FIG. 14), and may notice thromboembolism in these locations. The user may choose to utilize a clot retriever 174 to remove the embolus, or may simply allow physiological changes from the retrograde perfusion to clear the embolus. For example, the embolus may be pushed out into the internal carotid artery.

Although the right middle cerebral artery 43 has been used to illustrate the location of several cerebral interventions, any other artery around the Circle of Willis 29 may be the site of the interventions described herein. Although the approach through the right internal carotid artery 27 has been used to illustrate the arterial catheter pathway used herein, alternatively, the left internal carotid artery 25, the left or right vertebral arteries 31, 33 and basilar artery 35 approaches are also possible to access the Circle of Willis 29. The actual approach (or combination of more than one approach) used may depend on the location of the target site, and also may depend upon the amount of tortuosity in each vessel and ease of approach, and on the particular flow characteristics and flow direction(s). Cerebral interventions other than removal of emboli or thromboemboli are also possible in combination with the embodiments described herein. Such interventions may include embolization of cerebral aneurysms or arteriovenous malformations or cerebral stenting.

Figure 24:
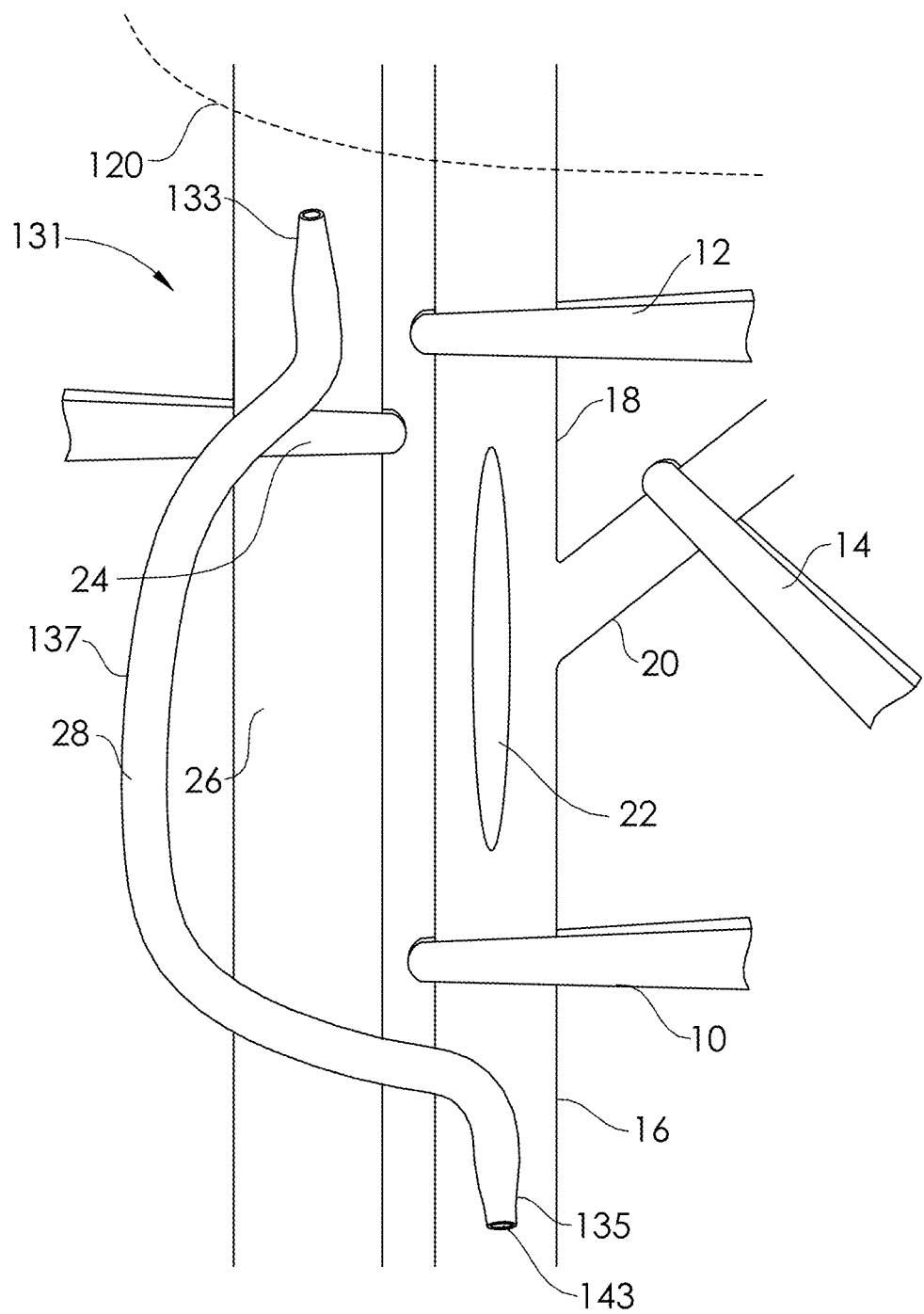
FIG. 24 illustrates a system for retrograde flow to cerebral vasculature, according to an embodiment of the present disclosure.

FIG. 24 illustrates a shunt catheter 28 prior to insertion into the vasculature of a patient 131 during a carotid endarterectomy procedure. The shunt catheter has a distal end 133, a proximal end 135, a shaft 137 extending between the distal end 133 and the proximal end 135, and a lumen 143 extending within the shaft 137 between the distal end 133 and the proximal end 135. The distal end 133 and the proximal end 135 may each include tapers, for improved insertion through skin and blood vessel walls, and into blood vessels, or for general atraumatic function. The user (e.g. vascular surgeon) applies a first occluding clamp 10 to the common carotid artery 16, a second occluding clamp 12 to the internal carotid artery 18, and a third occluding clamp 14 to the external carotid artery 20, to occlude the flow through each of these vessels. The user creates an opening 22 in the carotid artery (in this case extending between the common carotid artery 16 and the internal carotid artery 18). The user then applies a fourth occluding clamp 24 to the internal jugular vein 26 to prevent blood from flowing to the heart from this vessel. The shunt catheter 28 has an outer diameter and a lumen 143 diameter large enough to provide sufficient blood flow to the brain. In some embodiments, the shunt catheter may have a 6 French to 17 French diameter, or an 8 French to 14 French diameter.

Figure 25:
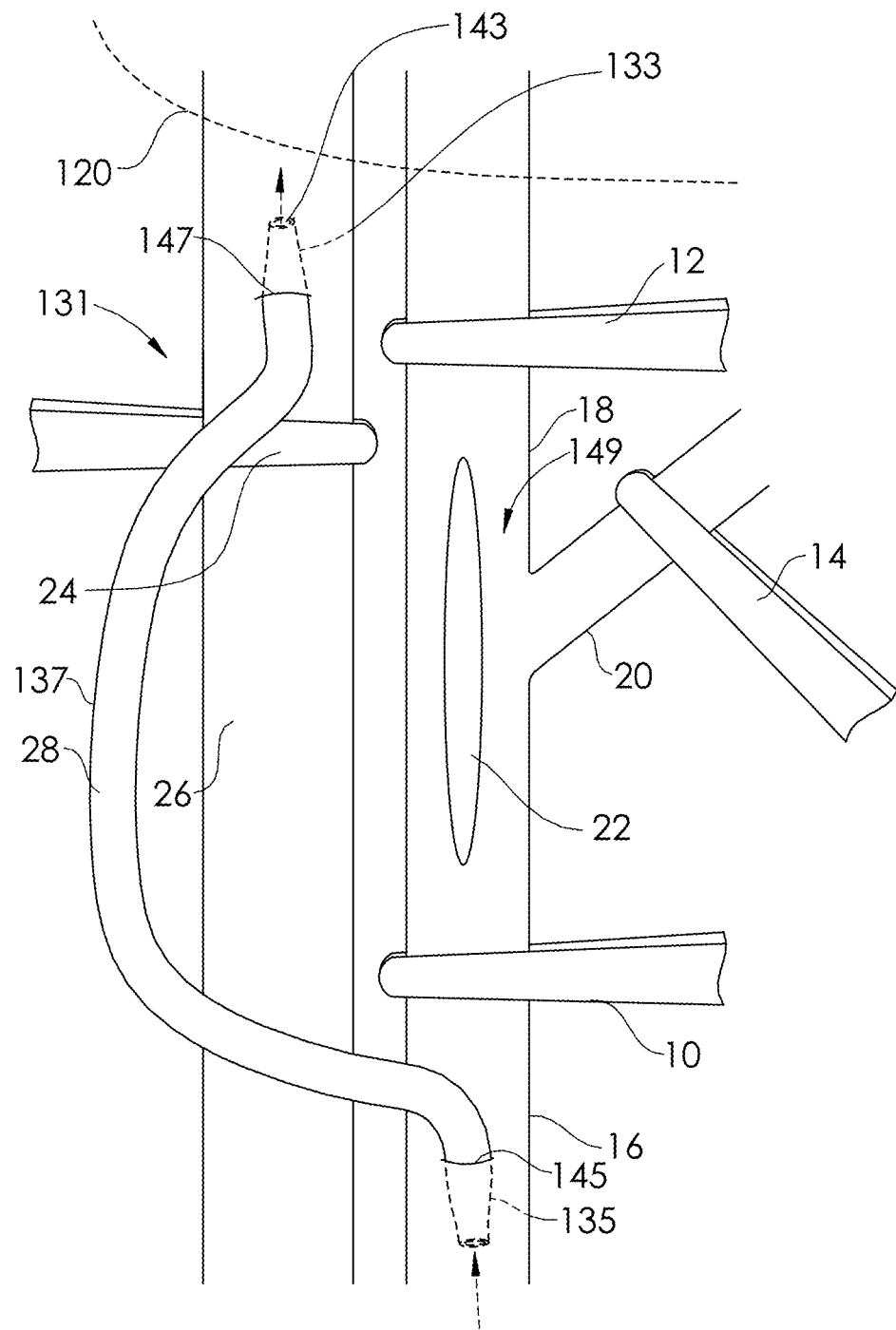
FIG. 25 illustrates the system of FIG. 24 while operating.

FIG. 25 illustrates the shunt catheter 28 after insertion into the patient 131. The proximal end 135 of the shunt catheter 28 is inserted through a puncture or incision 145 in the common carotid artery 16, proximal to the first occluding clamp 10, and the distal end 133 is inserted into a puncture or incision 147 in the internal jugular vein 26, distal to the fourth occluding clamp 24. Pressurized arterial (oxygenated) blood from the common carotid artery 16 is now able to flow through the lumen 143 from the proximal end 135 to the distal end 133 and out into internal jugular vein 26. The fourth occluding clamp 24, by occluding the internal jugular vein 16 proximal to the distal end 133 of the shunt catheter 28, assures that the blood can be delivered into the cerebral vasculature retrogradely, by the higher arterial pressure within the common carotid artery 16 (see arrows). The shunt catheter 28 may be placed such that the distal end 133 is at or near the base 120 of the skull of the patient 131. The two ends 133, 135 may stay in place simply from the frictional resistance of the outer surface of the shaft 137 through the openings 145, 147 in the blood vessels. However, the shunt catheter 28 may also be further secured in place by surgical tape, or tied to one or more of the blood vessels one or more sutures. Alternatively, the shunt catheter 28 may have suture wings attached adjacent the distal end 133 and/or the proximal end 135, or in between, and the suture wings may be sutured to the blood vessel wall, or adjoining tissue. In one embodiment, the proximal end 135 of the shunt catheter 28 is inserted into the opening 145 first, and then blood is allowed to flush through the lumen 143 until it exits the distal end 133. Then, the distal end 133 is inserted into the opening 147. In another embodiment, the lumen 143 is pre-flushed and primed with a syringe using, for example, sterile normal saline, and then the proximal end 135 and distal end 133 are inserted. The shunt catheter 28 is left in the position shown in FIG. 25 throughout the endarterectomy procedure, while atherosclerotic material and/or thrombus is removed from the internal wall of the carotid (common carotid artery 16 and/or internal carotid artery 18, depending on the extent of the disease). Thus, the general area 149 of the disease is protected by removing the flow and isolating the area with the first, second, and third clamps 10, 12, 14. Furthermore, the oxygenated blood from the common carotid artery 16 is able to perfuse the brain via the retrograde flow.

Though carotid shunts are often sized for fit into the internal carotid artery 18 (which tends to be smaller in diameter than the common carotid artery 16), there is traditionally some limit on catheter lumen size and the resulting flow rate of blood delivered therethrough. Under the embodiments described herein, if the distal end 133 is placed in the internal jugular vein 26, near the skull base 120, and the proximal end 135 is placed in the common carotid artery 16, the relatively large diameters of these vessels make possible the use of a large diameter, and large lumen, shunt catheter 28. The increase lumen 143 size further aids the delivery of sufficient flow rates of oxygenated blood to the cerebral circulation. A larger diameter shunt catheter 28 will often fit into the common carotid artery 16 than that which would be able to fit into the internal carotid artery 18. Furthermore, because the internal jugular vein 26 is commonly patulous and distensible, it will often also accommodate this larger shunt diameter than what is typically used. In one embodiment, a 12 French outer diameter shunt catheter 28 placed to extend from the common carotid artery 16 into the internal jugular vein 26 is configured to passively deliver blood at a flow rate of at least about 250 milliliters/min, depending upon patient pressure gradients, and in many cases is able to maintain adequate cerebral perfusion during ipsilateral (same side) internal carotid artery 18 occlusion. This flow rate may be achieved under a typical range of human cardiac output, with or without the effects of general anesthesia on the patient. At the end of the carotid endarterectomy procedure, the catheter 28 is removed from the internal jugular vein 26 and from the common carotid artery 16. In some embodiments, the user first removes the distal end 133 from the internal jugular vein 26 and then removes the proximal end 135 from the common carotid artery 16. The openings 145, 147 can now be closed with sutures, as can the opening 22. In some cases, one or both of the openings 145, 147 may not require a suture. The clamps 10, 12, 14, 24 can then be removed to restore normal antegrade flow.

Figure 26:
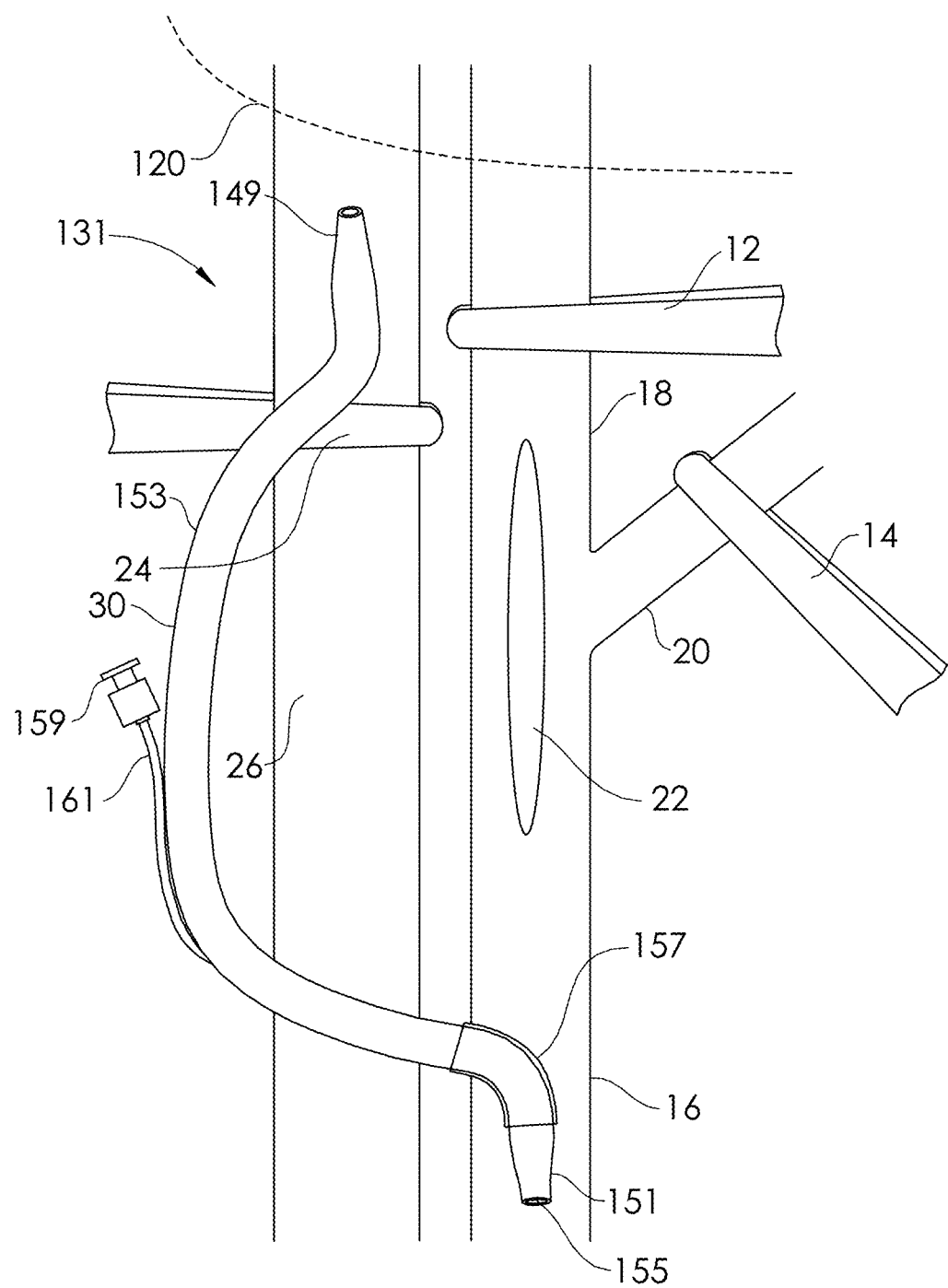
FIG. 26 illustrates a system for retrograde flow to cerebral vasculature, according to an embodiment of the present disclosure.

FIG. 26 illustrates a shunt catheter 30 prior to insertion into the vasculature of a patient 131 during a carotid endarterectomy procedure. The shunt catheter 30 has a distal end 149, a proximal end 151, a shaft 153 extending between the distal end 149 and the proximal end 151, and a lumen 155 extending within the shaft 153 between the distal end 149 and the proximal end 151. The distal end 149 and the proximal end 151 may each include tapers, for improved insertion through skin and blood vessel walls, and into blood vessels, or for general atraumatic function. The user (e.g. vascular surgeon) applies a first occluding clamp 12 to the internal carotid artery 18 and a second occluding clamp 14 to the external carotid artery 20, to occlude the flow through each of these vessels. The user creates an opening 22 in the carotid artery (in this case extending between the common carotid artery 16 and the internal carotid artery 18). The user then applies a third occluding clamp 24 to the internal jugular vein 26 to prevent blood from flowing to the heart from this vessel. The shunt catheter 30 has an outer diameter and a lumen 155 diameter large enough to provide sufficient blood flow to the brain. The shunt catheter 30 comprises an inflatable balloon 157 adjacent its proximal end 151. The balloon 151 is inflatable via a luer connector 159 which is hydraulically connected via an extension tube 161 and an inflation lumen 163. The inflatable balloon 157 is configured to be inflated within the interior of the common carotid artery 16 in order to occlude it. The balloon 157 may comprise an elastomer, such as latex, polyurethane, or a thermoplastic elastomer, such as polyether block amide.

Figure 27:
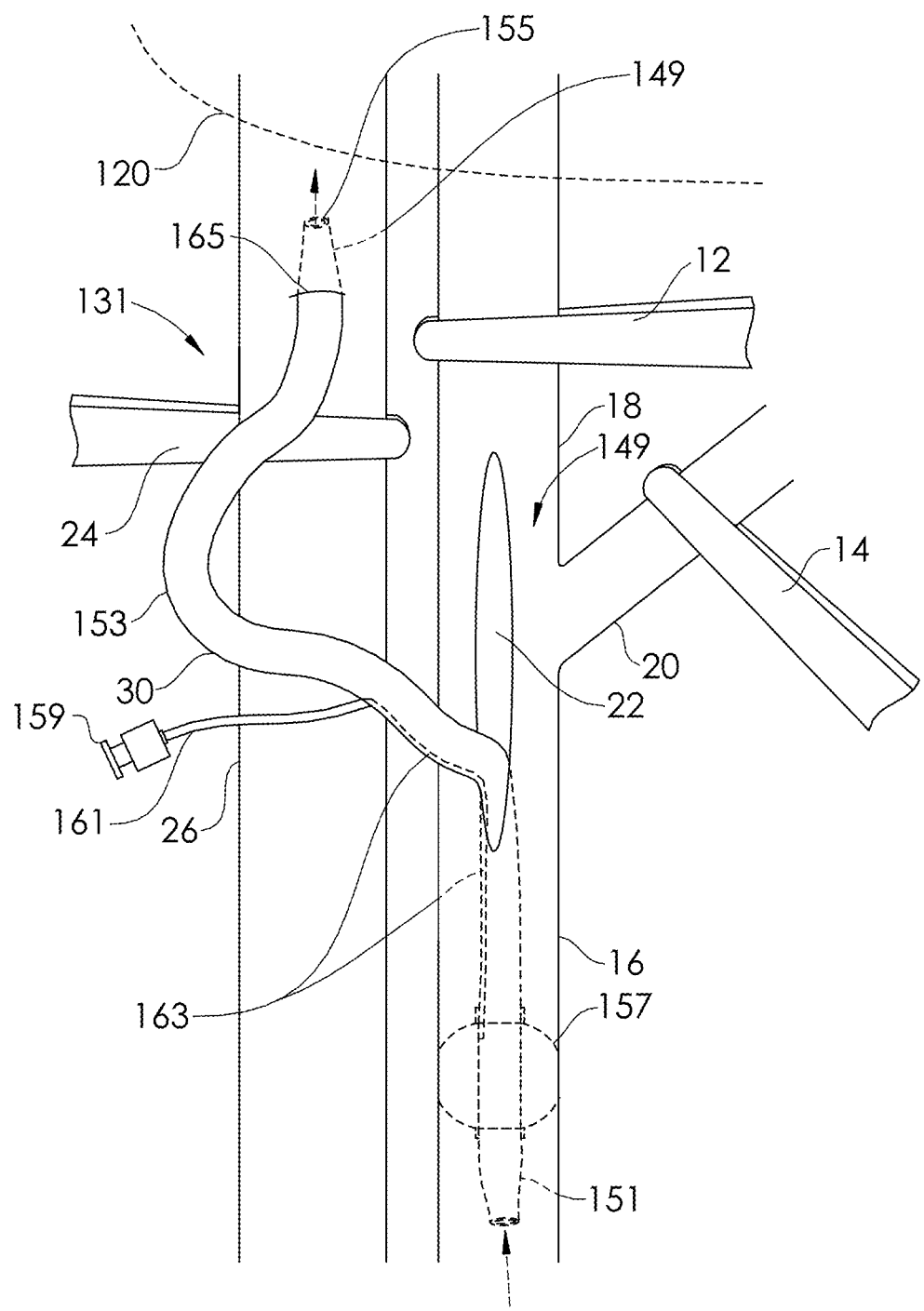
FIG. 27 illustrates the system of FIG. 26 while operating.

FIG. 27 illustrates the shunt catheter 30 after insertion into the patient 131. The proximal end 151 of the shunt catheter 30 is inserted into the opening 22, and the distal end 149 is inserted into a puncture or incision 165 in the internal jugular vein 26, distal to the third occluding clamp 24. The balloon 157 is inflated by applying pressure from a syringe or inflation device to the luer 159, thus occluding the common carotid artery 16 from the inside. Pressurized arterial (oxygenated) blood from the common carotid artery 16 is now able to flow through the lumen 155 from the proximal end 151 to the distal end 149 and out into internal jugular vein 26. The third occluding clamp 24, by occluding the internal jugular vein 16 proximal to the distal end 149 of the shunt catheter 30, assures that the blood can be delivered into the cerebral vasculature retrogradely, by the higher arterial pressure within the common carotid artery 16 (see arrows). The shunt catheter 30 may be placed such that the distal end 149 is at or near the base 120 of the skull of the patient 131. The distal end 149 may stay in place simply from the frictional resistance of the outer surface of the shaft 153 through the opening 165 in the internal jugular vein 26, and the proximal end 151 may stay in place simply from the frictional resistance of the inflated balloon 157 within the common carotid artery 16. However, the shunt catheter 30 may also be further secured in place by surgical tape, or tied to one or more of the blood vessels one or more sutures. Alternatively, the shunt catheter 30 may have suture wings attached adjacent the distal end 149 and/or the proximal end 151, or in between, and the suture wings may be sutured to the blood vessel wall, or adjoining tissue. In one embodiment, the proximal end 151 of the shunt catheter 30 is inserted into the opening 22 first, and the balloon 157 is inflated, and then blood is allowed to flush through the lumen 155 until it exits the distal end 149. Then, the distal end 149 is inserted into the opening 165. In another embodiment, the lumen 155 is pre-flushed and primed with a syringe using, for example, sterile normal saline, and then the proximal end 151 and distal end 149 are inserted. The shunt catheter 30 is left in the position shown in FIG. 27 throughout the endarterectomy procedure, while atherosclerotic material and/or thrombus is removed from the internal wall of the carotid (common carotid artery 16 and/or internal carotid artery 18, depending on the extent of the disease). Thus, the general area 149 of the disease is protected by removing the flow and isolating the area with the first and second clamps 12, 14, and the inflation of the balloon 157. Furthermore, the oxygenated blood from the common carotid artery 16 is able to perfuse the brain via the retrograde flow. At the end of the carotid endarterectomy procedure, the catheter 30 is removed from the internal jugular vein 26 and from the common carotid artery 16. In some embodiments, the user first removes the distal end 149 from the internal jugular vein 26 and then deflates the balloon 157, and removes the proximal end 151 from the common carotid artery 16. The opening 165 can now be closed with sutures, as can the opening 22. In some cases, the opening 165 may not require a suture. The clamps 12, 14, 24 can then be removed to restore normal antegrade flow.

Figure 28:
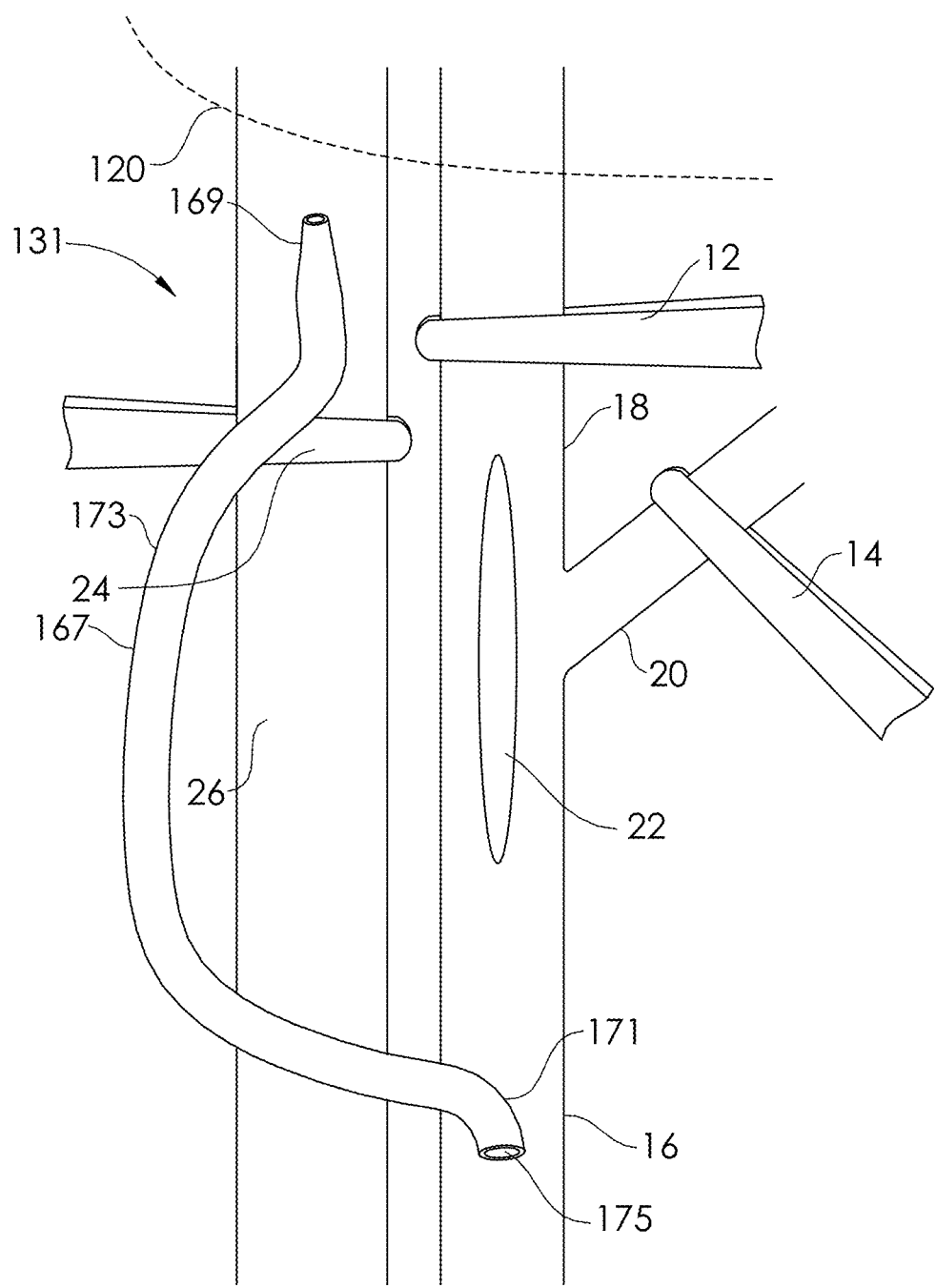
FIG. 28 illustrates a system for retrograde flow to cerebral vasculature, according to an embodiment of the present disclosure.

FIG. 28 illustrates a shunt catheter 167 prior to insertion into the vasculature of a patient 131 during a carotid endarterectomy procedure. The shunt catheter 167 has a distal end 169, a proximal end 171, a shaft 173 extending between the distal end 169 and the proximal end 171, and a lumen 175 extending within the shaft 173 between the distal end 169 and the proximal end 171. The distal end 169 and the proximal end 171 may each include tapers, for improved insertion through skin and blood vessel walls, and into blood vessels, or for general atraumatic function. In the shunt catheter 167 in FIG. 28 has little or no taper at its proximal end 171. The user (e.g. vascular surgeon) applies a first occluding clamp 12 to the internal carotid artery 18 and a second occluding clamp 14 to the external carotid artery 20, to occlude the flow through each of these vessels. The user creates an opening 22 in the carotid artery (in this case extending between the common carotid artery 16 and the internal carotid artery 18). The user then applies a third occluding clamp 24 to the internal jugular vein 26 to prevent blood from flowing to the heart from this vessel. The shunt catheter 167 has an outer diameter and a lumen 175 diameter large enough to provide sufficient blood flow to the brain.

Figure 29:
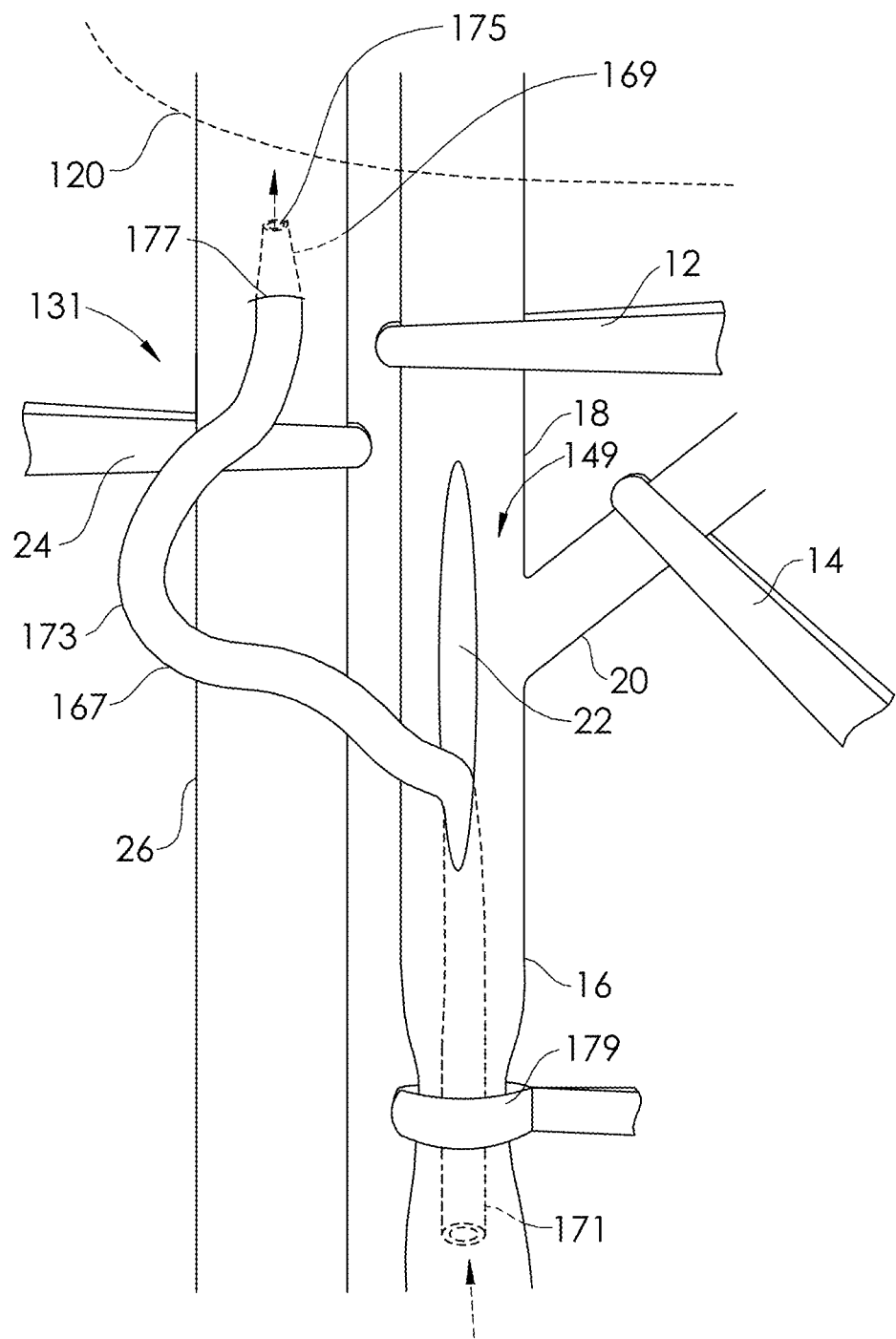
FIG. 29 illustrates the system of FIG. 28 while operating.

FIG. 29 illustrates the shunt catheter 167 after insertion into the patient 131. The proximal end 171 of the shunt catheter 167 is inserted into the opening 22, and the distal end 169 is inserted into a puncture or incision 177 in the internal jugular vein 26, distal to the third occluding clamp 24. A fourth occluding clamp 179, which may comprise a ring-shaped clamp, such as a Javid clamp, is clamped around the common carotid artery 16 over the proximal end 171 of the shunt catheter 167. Pressurized arterial (oxygenated) blood from the common carotid artery 16 is forced to flow through the lumen 175 from the proximal end 171 to the distal end 169 and out into internal jugular vein 26. The third occluding clamp 24, by occluding the internal jugular vein 16 proximal to the distal end 169 of the shunt catheter 167, assures that the blood can be delivered into the cerebral vasculature retrogradely, by the higher arterial pressure within the common carotid artery 16 (see arrows). The shunt catheter 167 may be placed such that the distal end 169 is at or near the base 120 of the skull of the patient 131. The distal end 169 may stay in place simply from the frictional resistance of the outer surface of the shaft 173 through the opening 177 in the internal jugular vein 26, and the proximal end 171 may stay in place simply from the clamping to the common carotid artery 16 by the fourth clamp 179. However, the shunt catheter 167 may also be further secured in place by surgical tape, or tied to one or more of the blood vessels one or more sutures. Alternatively, the shunt catheter 167 may have suture wings attached adjacent the distal end 169 and/or the proximal end 171, or in between, and the suture wings may be sutured to the blood vessel wall, or adjoining tissue. In one embodiment, the proximal end 171 of the shunt catheter 167 is inserted into the opening 22 first, and the fourth clamp 179 is secured, and then blood is allowed to flush through the lumen 175 until it exits the distal end 169. Then, the distal end 169 is inserted into the opening 177. In another embodiment, the lumen 175 is pre-flushed and primed with a syringe using, for example, sterile normal saline, and then the proximal end 171 and distal end 169 are inserted. The shunt catheter 167 is left in the position shown in FIG. 29 throughout the endarterectomy procedure, while atherosclerotic material and/or thrombus is removed from the internal wall of the carotid (common carotid artery 16 and/or internal carotid artery 18, depending on the extent of the disease). Thus, the general area 149 of the disease is protected by removing the flow and isolating the area with the first and second clamps 12, 14, and the fourth clamp 179. Furthermore, the oxygenated blood from the common carotid artery 16 is able to perfuse the brain via the retrograde flow. At the end of the carotid endarterectomy procedure, the catheter 167 is removed from the internal jugular vein 26 and from the common carotid artery 16. In some embodiments, the user first removes the distal end 169 from the internal jugular vein 26 and then unclamps the fourth clamp 179, and removes the proximal end 171 from the common carotid artery 16. The opening 177 can now be closed with sutures, as can the opening 22. In some cases, the opening 177 may not require a suture. The other clamps 12, 14, 24 can then be removed to restore normal antegrade flow. As shown in FIGS. 28-29, the proximal end 171 in some embodiments may be flush and not have any connector. Furthermore, in other embodiments, sideholes (not shown) may be added through the wall of the shaft 173 at the proximal end 171, in order to decrease fluid resistance of the entering blood.

The following clauses include examples of the disclosure:

Clause 1—A method for providing retrograde perfusion of a patient's brain includes occluding a carotid artery at a carotid occlusion location, occluding a jugular vein at a jugular occlusion location, and passively shunting arterial blood from a location in the carotid artery proximal to the carotid occlusion location to a location in the jugular vein distal to the jugular occlusion location.

Clause 2—The method of clause 1, wherein shunting includes inserting a proximal end of a catheter in the carotid artery and a distal end of the catheter in the jugular vein.

Clause 3—The method of clause 2, wherein occluding a carotid artery includes expanding a balloon carried on an exterior of the catheter at or adjacent the proximal end within the carotid artery.

Clause 4—The method of any one of clauses 1-3, wherein occluding a carotid artery includes applying a vascular clamp to an exterior surface of the carotid artery.

Clause 5—The method of any one of clauses 1-4, wherein occluding a carotid artery includes occluding an internal carotid artery.

Clause 6—The method of any one of clauses 1-5, wherein occluding a carotid artery includes occluding a common carotid artery.

Clause 7—The method of any one of clauses 1-6, wherein occluding a jugular vein includes applying a vascular clamp to an external surface of the jugular vein.

Clause 8—the method of any one of clauses 1-7, wherein occluding a jugular vein includes occluding an internal jugular vein.

Clause 9—the method of any one of clauses 1-8, wherein the carotid artery and the jugular vein are both on the same side of the patient's body.

Clause 10—the method of clause 2, wherein occluding a carotid artery includes applying a vascular clamp to an exterior surface of the carotid artery such that an internal portion of the carotid artery engages the proximal end of the catheter.

Clause 11—a shunt catheter includes a tubular shaft having a wall, a distal end having a tapered outer diameter, and a proximal end, the distal end configured for insertion into a jugular vein and the proximal end having an outer surface configured to engage an interior of a carotid artery when the carotid artery is clamped around the outer surface with a Javid clamp or the like, the proximal end further including an extreme flush termination.

Clause 12—the shunt catheter of clause 12, wherein the proximal end does not have any connector.

Clause 13—the shunt catheter of either one of clauses 11 or 12, further including one or more holes through the wall at the proximal end.

Clause 14—a shunt catheter includes a tubular shaft having a wall, a distal end having a tapered outer diameter, and a proximal end, the distal end configured for insertion into a jugular vein and the proximal end having an occlusion balloon carried thereon.

Clause 15—the shunt catheter of clause 14, further including a connector coupled at an intermediate portion of the shaft, and an inflation lumen extending between the connector and an interior of the balloon, the connector configured to coupled to a pressurization source for expanding the balloon.

Clause 16—the shunt catheter of either one of clauses 14 or 15, wherein the balloon includes an elastomer.

Clause 17—the shunt catheter of any one of clauses 11-16 further comprising a suture-holding structure configured to support suturing of the shaft to body tissue.

Clause 18—a shunt catheter includes a tubular shaft having a wall, a distal end having a tapered outer diameter, and a proximal end having a tapered outer diameter, the distal end configured for insertion into a jugular vein and the proximal end configured for insertion into a carotid artery, the catheter further including a suture-holding structure configured to support suturing of the shaft to body tissue.

Clause 19—the shunt catheter of any one of clauses 11-18, further including a perfusion lumen extending through the shaft, the perfusion lumen configured to provide a passive flow rate of at least about 250 ml per minute between the common carotid artery and the internal jugular vein at normal human cardiac output ranges.

Clause 20—the shunt catheter of clause 19, wherein the perfusion lumen is configured to provide a passive flow rate of at least about 250 ml per minute between the common carotid artery and the internal jugular vein at normal human cardiac output ranges when under general anesthesia.

While the methods described herein are intended to be performed at normothermia, alternatively the blood flowing (e.g., through extension tubes) outside of the patient can instead be heated with heat exchangers or other heaters to temperatures as high as 39° C. or potentially even higher. The hyperthermia that can be caused and maintained by reinjection and recirculation of heated blood may be able to cause some vasodilation, which may aid dislodgement of thrombus or flushing out of thrombus.

While the foregoing is directed to embodiments of the present disclosure, other and further embodiments may be devised without departing from the basic scope thereof.

The ranges disclosed herein also encompass any and all overlap, sub-ranges, and combinations thereof. Language such as "up to," "at least," "greater than," "less than," "between," and the like includes the number recited. Numbers preceded by a term such as "approximately", "about", and "substantially" as used herein include the recited numbers (e.g., about 10%=10%), and also represent an amount close to the stated amount that still performs a desired function or achieves a desired result. For example, the terms "approximately", "about", and "substantially" may refer to an amount that is within less than 10% of, within less than 5% of, within less than 1% of, within less than 0.1% of, and within less than 0.01% of the stated amount.

For purposes of the present disclosure and appended claims, the conjunction "or" is to be construed inclusively (e.g., "an apple or an orange" would be interpreted as "an apple, or an orange, or both"; e.g., "an apple, an orange, or an avocado" would be interpreted as "an apple, or an orange, or an avocado, or any two, or all three"), unless: (i) it is explicitly stated otherwise, e.g., by use of "either . . . or," "only one of," or similar language; or (ii) two or more of the listed alternatives are mutually exclusive within the particular context, in which case "or" would encompass only those combinations involving non-mutually-exclusive alternatives. For purposes of the present disclosure and appended claims, the words "comprising," "including," "having," and variants thereof, wherever they appear, shall be construed as open-ended terminology, with the same meaning as if the phrase "at least" were appended after each instance thereof.

What is claimed is:

1. A method of providing retrograde perfusion of a patient's brain, the method comprising:
    occluding a jugular vein of a subject at a jugular occlusion location;
    advancing a first end of a catheter into the jugular vein, the catheter having a lumen extending therethrough;
    advancing a second end of the catheter into an artery of the subject; and
    passively shunting arterial blood from the artery of the subject to a location in the jugular vein distal to the jugular occlusion location.

2. The method of claim 1, wherein passively shunting arterial blood comprises passively shunting the arterial blood from a carotid artery of the subject through the lumen to the location in the jugular vein distal to the jugular occlusion location.

3. The method of claim 1, wherein the jugular vein comprises an internal jugular vein.

4. The method of claim 1, wherein at least some of the passively shunted arterial blood retrogradely perfuses at least some brain tissue of the subject.

5. The method of claim 1, wherein occluding the jugular vein comprises applying a vascular clamp to the jugular vein.

6. The method of claim 1, wherein occluding the jugular vein comprises expanding within the jugular vein a balloon carried on the catheter.

7. The method of claim 1, further comprising occluding the artery at an artery occlusion location.

8. The method of claim 7, wherein occluding the artery comprises applying a vascular clamp to the artery.

9. The method of claim 7, wherein occluding the artery comprises expanding within the artery a balloon carried on the catheter.

10. A method of providing retrograde perfusion of a patient's brain, the method comprising:
    occluding a jugular vein of a subject at a jugular occlusion location;
    advancing a first end of a catheter into the jugular vein, the catheter having a lumen extending therethrough;
    advancing a second end of the catheter into an artery of the subject; and
    selectively introducing arterial blood from the artery of the subject into the jugular vein distal to the jugular occlusion location such that a pressure gradient from the artery to the jugular vein causes retrograde flow within the jugular vein.

11. The method of claim 10, wherein selectively introducing arterial blood comprises passively shunting the arterial blood from a carotid artery of the subject through the lumen to the location in the jugular vein distal to the jugular occlusion location.

12. The method of claim 10, wherein at least some of the passively shunted arterial blood retrogradely perfuses at least some brain tissue of the subject.

13. The method of claim 10, wherein the jugular vein comprises an internal jugular vein.

14. The method of claim 10, wherein occluding the jugular vein comprises applying a vascular clamp to the jugular vein.

15. The method of claim 10, wherein occluding the jugular vein comprises expanding within the jugular vein a balloon carried on the catheter.

16. The method of claim 10, further comprising occluding the artery at an artery occlusion location.

17. The method of claim 16, wherein occluding the artery comprises applying a vascular clamp to the artery.

18. The method of claim 16, wherein occluding the artery comprises expanding within the artery a balloon carried on the catheter.

* * * * *